US006287813B1

(12) United States Patent
Fussenegger et al.

(10) Patent No.: US 6,287,813 B1
(45) Date of Patent: Sep. 11, 2001

(54) ANTIBIOTIC-BASED GENE REGULATION SYSTEM

(75) Inventors: Martin Fussenegger, Zürich; Charles J. Thompson, Binningen; James E. Bailey, Zürich, all of (CH)

(73) Assignee: Cistronics Cell Technology GmbH, Zurich (CH)

( * ) Notice: Subject to any disclaimer, the term of this patent is extended or adjusted under 35 U.S.C. 154(b) by 0 days.

(21) Appl. No.: 09/411,687

(22) Filed: Oct. 4, 1999

Related U.S. Application Data

(63) Continuation-in-part of application No. 09/298,768, filed on Apr. 23, 1999, now abandoned.
(51) Int. Cl.[7] .......................... C12N 15/09; C12N 15/00; C12N 15/79; C12N 5/00; C07H 21/04
(52) U.S. Cl. .................... 435/69.1; 435/69.7; 435/375; 435/320.1; 435/325; 435/455; 536/23.1; 536/23.4
(58) Field of Search .................... 435/69.1, 375, 435/69.7, 320.1, 455, 325; 536/23.1, 23.4

(56) References Cited

U.S. PATENT DOCUMENTS

| | | |
|---|---|---|
| 5,464,758 | 11/1995 | Gossen et al. . |
| 5,514,578 | 5/1996 | Hogness et al. . |
| 5,589,362 | 12/1996 | Bujard et al. . |
| 5,650,298 | 7/1997 | Bujard et al. . |
| 5,654,168 | 8/1997 | Bujard et al. . |
| 5,674,730 | 10/1997 | Baim et al. . |
| 5,686,574 | 11/1997 | Moore et al. . |
| 5,789,156 | 8/1998 | Bujard et al. . |
| 5,866,755 | 2/1999 | Bujard et al. . |
| 5,885,779 * | 3/1999 | Sadowski et al. ............... 435/6 |
| 5,888,981 | 3/1999 | Bujard et al. . |

OTHER PUBLICATIONS

Tim Clackson, Current Opinions in Chemical Biology, vol. 4, No. 15, pp. 1907–1914, 1997.*
U.S application No. 08/948,381, filed Oct. 9, 1997.
August et al., 1998, "Biosynthesis of the ansamycin antibiotic rifamycin: deductions from the molecular analysis of the rif biosynthetic gene cluster of *Amycolatopsis mediterranei* S699," *Chemistry and Biology* 5:69–79.
Bébéar and Bouanchaud, 1997, "A review of the in–vitro activity of quinupristin/dalfopristin against intracellular pathogens and mycoplasmas," *J. Antimicrob. Chemother.* 39(Suppl. A):59–62.
Bergeron and Montay, 1997, "The pharmacokinetics of quinupristin/dalfopristin in laboratory animals and in humans," *J. Antimicrob. Chemother.* 39(Suppl. A):129–138.
Blanc et al., 1995, "Molecular characterization and transcriptional analysis of a multidrug resistance gene cloned from the pristinamycin–producing organism, *Streptomyces pristinaespiralis*," *Mol. Microbiol.* 17(5):989–999.

Bohl et al., 1997, "Long–term control of erythropoietin secretion by doxycycline in mice transplanted with engineered primary myoblasts," *Nature Medicine* 3(3):299–305.
Clackson, 1997, "Controlling mammalian gene expression with small molecules," *Current Opinions in Chemical Biology* 1:210–218.
Deuschle et al., 1995, "Tetracycline–Reversible Silencing of Eukaryotic Promoters," *Molecular and Cellular Biology* 15(4):1907–1914.
Fernandez–Moreno et al., 1991, "The act Cluster Contains Regulatory and Antibiotic Export Genes, Direct Targets for Translational Control by the bldA tRNA Gene of Streptomyces," *Cell* 66:769–780.
Furuya and Hutchinson, 1996, "The DnrN Protein *Streptomyces peucetius*, a Pseudo–Response Regulator, Is a DNA–Binding Protein Involved in the Regulation of Daunorubicin Biosynthesis," *Journal of Bacteriology* 178:6310–6318.
Fussenegger et al., 1998, "Controlled proliferation by multigene metabolic engineering enhances the productivity of Chinese hamster ovary cells," *Nat. Biotechnol.* 16:468–471.
Fussenegger et al., 1998 "pTrident, a Novel Vector Family for Tricistronic Gene Expression in Mammalian Cells," *Biotechnol. Bioeng.* 57:1–10.
Fussenegger et al., 1997, "A Novel Cytostatic Process Enhances the Productivity of Chinese Hamster Ovary Cells," *Biotechnol. Bioeng.* 55:927–939.
Fussenegger et al., 1997, "Autoregulated Multicistronic Expression Vectors Provide One–Step Cloning of Regulated Product Gene Expression in Mammalian Cells," *Biotechnol. Prog.* 13:733–740.
Gari et al., 1997, "A Set of Vectors with a Tetracycline––Regulatable Promotor System for Modulated Gene Expression in *Saccharomyces cerevisiae*, " *Yeast* 13:837–848.
Gossen et al., 1995, "Transcriptional Activation by Tetracyclines in Mammalian Cells," *Science* 268:1766–1769.
Guilfoile and Hutchinson, 1992, "The *Streptomyces glaucescens* TcmR Protein Represses Transcription of the Divergently Oriented tcmR and tcmA Genes by Binding to an Intergenic Operator Region," *Journal of Bacteriology* 174(11):3659–3666.

(List continued on next page.)

*Primary Examiner*—David Guzo
*Assistant Examiner*—Gerald G. Leffers, Jr.
(74) *Attorney, Agent, or Firm*—Pennie & Edmonds LLP

(57) ABSTRACT

The invention relates to a novel system for gene regulation in eukaryotic cells, and methods of using the same for protein production, tissue engineering and gene therapy. In particular, the invention provides a new system for antibiotic-regulated gene expression in eukaryotic cells based on sequences from Actinomycetes antibiotic resistance promoters, polypeptides that bind to the same in an antibiotic responsive manner, and nucleotides encoding such polypeptides. Further, the invention provides novel and sensitive methods of screening for candidate antibiotics.

25 Claims, 10 Drawing Sheets

OTHER PUBLICATIONS

Rossant and Nagy, 1999, "In search of the tabula rasa of human cells," *Nat. Biotechnol.* 17(1):23–24.

Salah–Bey et al., 1995, "Stress–activated expression of a *Streptomyces pristinaespiralis* multidrug resistance gene (ptr) in various *Streptomyces spp. and Escherichia coli*, " *Mol. Microbiol.* 17(5): 001–1012.

Salah–Bey et al., 1995, "Unusual regulatory mechanism for a *Streptomyces* multidrug resistance gene, ptr, involving three homologous protein–binding sites overlapping the promoter region," *Mol. Microbiol.* 17(6):1109–1119.

Schwecke et al., 1995, "The biosynthetic gene cluster for the polyketide immunosuppressant rapamycin," *Proc. Natl. Acad. Sci. U.S.A.* 92:7839–7843.

Sezonov et al., 1997, "Complete conversion of antibiotic precursor to pristinamycin IIA by overexpression of *Streptomyces pristinaespiralis* biosynthesis genes," *Nature Biotechnology* 15:349–353.

Solter and Gearhart, "Putting Stem Cells to Work," *Science* 283:1468–1470.

Westrich et al., 1999, "Cloning and Characterizatio of a gene cluster form *Streptomyces cyanogenus* S136 probably involved in landomycin biosynthesis," *FEMS Microbiology Letters* 170:381–387.

\* cited by examiner

SEQUENCE LISTING

<160> NUMBER OF SEQ ID NOS: 31

<210> SEQ ID NO 1
<211> LENGTH: 33
<212> TYPE: DNA
<213> ORGANISM: Artificial Sequence
<220> FEATURE:
<223> OTHER INFORMATION: Primer

<400> SEQUENCE: 1
gtacgaattc ccaccatgag tcgaggagag gtg                                33

<210> SEQ ID NO 2
<211> LENGTH: 35
<212> TYPE: DNA
<213> ORGANISM: Artificial Sequence
<220> FEATURE:
<223> OTHER INFORMATION: Primer

<400> SEQUENCE: 2
gcgcgcggct gtacgcggag gcctgttcga ccatc                              35

<210> SEQ ID NO 3
<211> LENGTH: 453
<212> TYPE: DNA
<213> ORGANISM: Streptomyces coelicolor

<400> SEQUENCE: 3
gatcgacgtc ggagaaatag cgctgtacag cgtatgggaa tctcttgtac ggtgtacgag     60
tatcttcccg tacaccgtac aaggagcctg cagggagtac cctcgaccgc cggagtataa    120
atagaggcgc ttcgtctacg gagcgacaat tcaattcaaa caagcaaagt gaacacgtcg    180
ctaagcgaaa gctaagcaaa taaacaagcg cagctgaaca agctaaacaa tctgcagtaa    240
agtgcaagtt aaagtgaatc aattaaaagt aaccagcaac caagtaaatc aactgcaact    300
actgaaatct gccaagaagt aattattgaa tacaagaaga gaactctgaa tactttcaac    360
aagttaccga gaaagaagaa ctcacacaca gctagcgttt aaacttaagc ttggtaccga    420
gctcggatcc actagtccag tgtggtggaa ttc                                453

<210> SEQ ID NO 4
<211> LENGTH: 1167
<212> TYPE: DNA
<213> ORGANISM: Artificial Sequence
<220> FEATURE:
<223> OTHER INFORMATION: Hybrid sequence

<400> SEQUENCE: 4
atgagtcgag gagaggtgcg catggcgaag gcagggcggg aggggccgcg ggacagcgtg     60
tggctgtcgg gggaggggcg cgcggcggt cgccgtgggg ggcagccgtc cgggctcgac     120
cgggaccgga tcaccggggt caccgtccgg ctgctggaca cggagggcct gacgggttc    180 tcgatgcgcc gcctggccgc cgagctgaac gtcaccgcga tgtccgtgta ctggtacgtc    240
gacaccaagg accagttgct cgagctgccc ctggacgccg tcttcggcga gctgcgccac    300
ccggacccgg acgccgggct cgactggcgc gaggaactgc gggccctggc cgggagaac    360 cgggcgctgc tggtgcgcca cccctggtcg tcccggctgg tcggcaccta cctcaacatc    420
ggcccgcact cgctggcctt ctcccgcgcg gtgcagaacg tcgtgcgccg cagcgggctg    480
cccgcgcacc gcctgaccgg cgccatctcg gccgtcttcc agttcgtcta cggctacggc    540

```
accatcgagg gccgcttcct cgcccggtg gcggacaccg ggctgagtcc ggaggagtac      600
ttccaggact cgatgaccgc ggtgaccgag gtgccggaca ccgcgggcgt catcgaggac      660
gcgcaggaca tcatggcggc ccggggcggc gacaccgtgg cggagatgct ggaccgggac      720
ttcgagttcg ccctcgacct gctcgtcgcg ggcatcgacg cgatggtcga acaggcctcc      780
gcgtacagcc gcgcgcgtac gaaaaacaat tacgggtcta ccatcgaggg cctgctcgat      840
ctcccggacg acgacgcccc cgaagaggcg gggctggcgg ctccgcgcct gtcctttctc      900 ccgcgggac acacgcgcag actgtcgacg gccccccga ccgatgtcag cctggggac       960 gagctccact tagacggcga ggacgtggcg atggcgcatg ccgacgcgct agacgatttc     1020
gatctggaca tgttgggga cggggattcc ccgggtccgg gatttacccc ccacgactcc     1080
gccccctacg gcgctctgga tatggccgac ttcgagtttg agcagatgtt taccgatgcc     1140
cttggaattg acgagtacgg tgggtag                                        1167

<210> SEQ ID NO 5
<211> LENGTH: 69
<212> TYPE: DNA
<213> ORGANISM: Artificial Sequence
<220> FEATURE:
<223> OTHER INFORMATION: Primer

<400> SEQUENCE: 5
cttgtacggt gtacgagtat cttcccgtac accgtacaag gagcctgcag ggagtaccct      60
cgaccgccg                                                              69

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
gatccatcga ttgatcaggc gc                                               22

<210> SEQ ID NO 7
<211> LENGTH: 64
<212> TYPE: DNA
<213> ORGANISM: Artificial Sequence
<220> FEATURE:
<223> OTHER INFORMATION: Primer

<400> SEQUENCE: 7
gatcgacgtc ggagaaatag cgctgtacag cgtatgggaa tctcttgtac ggtgtacgag      60
tatc                                                                   64

<210> SEQ ID NO 8
<211> LENGTH: 35
<212> TYPE: DNA
<213> ORGANISM: Artificial Sequence
<220> FEATURE:
<223> OTHER INFORMATION: Primer

<400> SEQUENCE: 8
gatcactagt gatatcgcta gctgtgtgtg agttc                                 35

<210> SEQ ID NO 9
<211> LENGTH: 82
<212> TYPE: DNA
```

<213> ORGANISM: Artificial Sequence
<220> FEATURE:
<223> OTHER INFORMATION: Primer

<400> SEQUENCE: 9
gatcggatcc atcgataata aaatatcttt attttcatta catctgtgtg ttggtttttt    60
gtgtgcgtcg agaaatagc gc    82

<210> SEQ ID NO 10
<211> LENGTH: 40
<212> TYPE: DNA
<213> ORGANISM: Artificial Sequence
<220> FEATURE:
<223> OTHER INFORMATION: Primer

<400> SEQUENCE: 10
gatcgatatc actagtcgcc accatgccca agaagaagcc    40

<210> SEQ ID NO 11
<211> LENGTH: 34
<212> TYPE: DNA
<213> ORGANISM: Artificial Sequence
<220> FEATURE:
<223> OTHER INFORMATION: Primer

<400> SEQUENCE: 11
gatcggatcc acgcgttcag atgctggcag cgtg    34

<210> SEQ ID NO 12
<211> LENGTH: 34
<212> TYPE: DNA
<213> ORGANISM: Artificial Sequence
<220> FEATURE:
<223> OTHER INFORMATION: Primer

<400> SEQUENCE: 12
gatcgaattc aagcttgcgg tcgtgcagac ccgg    34

<210> SEQ ID NO 13
<211> LENGTH: 37
<212> TYPE: DNA
<213> ORGANISM: Artificial Sequence
<220> FEATURE:
<223> OTHER INFORMATION: Primer

<400> SEQUENCE: 13
atgcatcgat gcggccgctt acgtttgacg tcttctg    37

<210> SEQ ID NO 14
<211> LENGTH: 78
<212> TYPE: DNA
<213> ORGANISM: Artificial Sequence
<220> FEATURE:
<223> OTHER INFORMATION: Primer

<400> SEQUENCE: 14
gatcgcggcc gcaataaaat atctttattt tcattacatc tgtgtgttgg ttttttgtgt    60
gcgtcggaga aatagcgc    78

<210> SEQ ID NO 15
<211> LENGTH: 28
<212> TYPE: DNA
<213> ORGANISM: Artificial Sequence
<220> FEATURE:
<223> OTHER INFORMATION: Primer

<400> SEQUENCE: 15
gtacagatct ttatttgtag agctcatc                                              28

<210> SEQ ID NO 16
<211> LENGTH: 64
<212> TYPE: DNA
<213> ORGANISM: Artificial Sequence
<220> FEATURE:
<223> OTHER INFORMATION: Primer

<400> SEQUENCE: 16
gatcgaattc cctcagcacc aggtcatgct taagtcgcga catatggatc cgctagcgct          60
accg                                                                        64

<210> SEQ ID NO 17
<211> LENGTH: 111
<212> TYPE: DNA
<213> ORGANISM: Artificial Sequence
<220> FEATURE:
<223> OTHER INFORMATION: Primer

<400> SEQUENCE: 17
gatcaagctt gcccgggcca cacaaaaaac caacacacag atgtaatgaa aataaagata          60
ttttatttga tcaggcgcgc cgcggccgca tgcttacttg tacagctcgt c                  111

<210> SEQ ID NO 18
<211> LENGTH: 66
<212> TYPE: DNA
<213> ORGANISM: Artificial Sequence
<220> FEATURE:
<223> OTHER INFORMATION: Primer

<400> SEQUENCE: 18
gtacgaattc gatatcatgc atggcgccgt ttaaacgcgt atttaaatga tccgctagcg          60
ctaccg                                                                      66

<210> SEQ ID NO 19
<211> LENGTH: 135
<212> TYPE: DNA
<213> ORGANISM: Artificial Sequence
<220> FEATURE:
<223> OTHER INFORMATION: Primer

<400> SEQUENCE: 19
gatcaagctt gcggccgcgg atccgcccgg gccacacaaa aaccaacac acagatgtaa          60 tgaaaataaa gatattttat tatcgatact agtgcgatcg cttaattaat ttaaatttac        120
ttgtacagct cgtcc                                                          135

<210> SEQ ID NO 20
<211> LENGTH: 154
<212> TYPE: DNA
<213> ORGANISM: Artificial Sequence
<220> FEATURE:
<223> OTHER INFORMATION: Synthetic sequence

<400> SEQUENCE: 20
gacgtcgata tcgaaatagc gctgtacagc gtatgggaat ctcttgtacg gtgtacgagt         60
atcttcccgt acaccgtacg aaatagcgct gtacagcgta tgggaatctc ttgtacggtg        120
tacgagtatc ttcccgtaca ccgtaccctg cagg                                    154

```
<210> SEQ ID NO 21
<211> LENGTH: 221
<212> TYPE: DNA
<213> ORGANISM: Artificial Sequence
<220> FEATURE:
<223> OTHER INFORMATION: Synthetic

<400> SEQUENCE: 21
gacgtcgata tcgaaatagc gctgtacagc gtatgggaat ctcttgtacg gtgtacgagt      60
atcttcccgt acaccgtacg aaatagcgct gtacagcgta tgggaatctc ttgtacggtg     120
tacgagtatc ttcccgtaca ccgtacgaaa tagcgctgta cagcgtatgg gaatctcttg     180
tacggtgtac gagtatcttc ccgtacaccg taccctgcag g                         221

<210> SEQ ID NO 22
<211> LENGTH: 27
<212> TYPE: DNA
<213> ORGANISM: Artificial Sequence
<220> FEATURE:
<223> OTHER INFORMATION: Primer

<400> SEQUENCE: 22
gatcgcgcgc atgatgagtt tcccacc                                          27

<210> SEQ ID NO 23
<211> LENGTH: 34
<212> TYPE: DNA
<213> ORGANISM: Artificial Sequence
<220> FEATURE:
<223> OTHER INFORMATION: Primer

<400> SEQUENCE: 23
gatcaagctt ggatccttag gagctgatct gact                                  34

<210> SEQ ID NO 24
<211> LENGTH: 1374
<212> TYPE: DNA
<213> ORGANISM: Artificial Sequence
<220> FEATURE:
<223> OTHER INFORMATION: Hybrid sequence

<400> SEQUENCE: 24
atgagtcgag gagaggtgcg catggcgaag gcagggcggg aggggccgcg ggacagcgtg      60
tggctgtcgg gggaggggcg gcgcggcggt cgccgtgggg ggcagccgtc cgggctcgac     120
cgggaccgga tcaccggggt caccgtccgg ctgctggaca cggagggcct gacggggttc     180
tcgatgcgcc gcctggccgc cgagctgaac gtcaccgcga tgtccgtgta ctggtacgtc     240
gacaccaagg accagttgct cgagctcgcc ctggacgccg tcttcggcga gctgcgccac     300
ccggacccgg acgccgggct cgactggcgc gaggaactgc gggccctggc ccgggagaac     360
cgggcgctgc tggtgcgcca ccctggtcg tcccggctgg tcggcaccta cctcaacatc     420
ggcccgcact cgctggcctt ctcccgcgcg gtgcagaacg tcgtgcgccg cagcgggctg     480
cccgcgcacc gcctgaccgg cgccatctcg gccgtcttcc agttcgtcta cggctacggc     540
accatcgagg gccgcttcct cgcccgggtg cgggacaccg gctgagtcc ggaggagtac     600 ttccaggact cgatgaccgc ggtgaccgag gtgccggaca ccgcgggcgt catcgaggac     660
gcgcaggaca tcatgcggc ccggggcggc gacaccgtgg cggagatgct ggaccgggac     720
ttcgagttcg ccctcgacct gctcgtcgcg ggcatcgacg cgatggtcga acaggcctcc     780
gcgtacagcc gcgcgcatga tgagtttccc accatggtgt tccttctgg gcagatcagc     840
```

```
caggcctcgg ccttggcccc ggcccctccc caagtcctgc cccaggctcc agcccctgcc      900
cctgctccag ccatggtatc agctctggcc caggccccag ccctgtccc agtcctagcc       960 ccaggccctc ctcaggctgt ggccccacct gcccccaagc ccaccaggc tggggaagga      1020 acgctgtcag aggccctgct gcagctgcag tttgatgatg aagacctggg ggccttgctt     1080
ggcaacagca cagacccagc tgtgttcaca gacctggcat ccgtcgacaa ctccgagttt     1140
cagcagctgc tgaaccaggg catacctgtg gccccccaca caactgagcc catgctgatg     1200
gagtaccctg aggctataac tcgcctagtg acagggccc agaggccccc cgacccagct      1260
cctgctccac tgggggcccc ggggctcccc aatggcctcc tttcaggaga tgaagacttc     1320
tcctccattg cggacatgga cttctcagcc ctgctgagtc agatcagctc ctaa           1374
```

<210> SEQ ID NO 25
<211> LENGTH: 101
<212> TYPE: DNA
<213> ORGANISM: Artificial Sequence
<220> FEATURE:
<223> OTHER INFORMATION: Primer

<400> SEQUENCE: 25

```
gatcgcgcgc cagatccaaa aagaagaga aggtagatc caaaagaag agaaaggtag         60 atccaaaaaa gaagagaaag gtaatggatg ctaagtcact a                        101
```

<210> SEQ ID NO 26
<211> LENGTH: 37
<212> TYPE: DNA
<213> ORGANISM: Artificial Sequence
<220> FEATURE:
<223> OTHER INFORMATION: Primer

<400> SEQUENCE: 26

```
gatcaagctt ggatccttac cagagatcat tccttgc                              37
```

<210> SEQ ID NO 27
<211> LENGTH: 1239
<212> TYPE: DNA
<213> ORGANISM: Artificial Sequence
<220> FEATURE:
<223> OTHER INFORMATION: Hybrid sequence

<400> SEQUENCE: 27

```
atgagtcgag gagaggtgcg catggcgaag gcagggcggg aggggccgcg ggacagcgtg      60
tggctgtcgg gggagggggcg gcgcggcggt cgccgtgggg ggcagccgtc cgggctcgac    120
cgggaccgga tcaccggggt caccgtccgg ctgctggaca cggagggcct gacggggttc     180
tcgatgcgcc gcctggccgc cgagctgaac gtcaccgcga tgtccgtgta ctggtacgtc     240
gacaccaagg accagttgct cgagctcgcc ctggacgccg tcttcggcga gctgcgccac     300
ccggacccgg acgccgggct cgactggcgc gaggaactgc gggccctggc ccgggagaac     360
cgggcgctgc tggtgcggcca cccctggtcg tcccggctgg tcggcaccta cctcaacatc     420
ggcccgcact cgctggcctt ctcccgcgcg gtgcagaacg tcgtgcgccg cagcgggctg      480
cccgcgcacc gctgaccgg cgccatctcg gccgtcttcc agttcgtcta cggctacggc      540
accatcgagg gccgcttcct cgcccgggtg gcggacaccg gctgagtcc ggaggagtac      600 ttccaggact cgatgaccgc ggtgaccgag gtgccggaca ccgcgggcgt catcgaggac     660
gcgcaggaca tcatggcggc ccggggcggc gacaccgtgg cggagatgct ggaccgggac     720
```

```
ttcgagttcg ccctcgacct gctcgtcgcg ggcatcgacg cgatggtcga acaggcctcc    780
gcgtacagcc gcgcgccaga tccaaaaaag aagagaaagg tagatccaaa aagaagaga     840 aaggtagatc caaaaaagaa gagaaaggta atggatgcta agtcactaac tgcctggtcc    900
cggacactgg tgaccttcaa ggatgtattt gtggacttca ccagggagga gtggaagctg    960
ctggacactg ctcagcagat cgtgtacaga aatgtgatgc tggagaacta taagaacctg   1020
gtttccttgg gttatcagct tactaagcca gatgtgatcc tccggttgga agggagaa     1080 gagccctggc tggtggagag agaaattcac caagagaccc atcctgattc agagactgca   1140
tttgaaatca aatcatcagt ttccagcagg agcattttta aagataagca atcctgtgac   1200
attaaaatgg aaggaatggc aaggaatgat ctctggtaa                          1239
```

<210> SEQ ID NO 28
<211> LENGTH: 29
<212> TYPE: DNA
<213> ORGANISM: Artificial Sequence
<220> FEATURE:
<223> OTHER INFORMATION: Primer

<400> SEQUENCE: 28

```
gatcaagctt tcaggcctgt tcgaccatc                                       29
```

<210> SEQ ID NO 29
<211> LENGTH: 780
<212> TYPE: DNA
<213> ORGANISM: Streptomyces coelicolor

<400> SEQUENCE: 29

```
atgagtcgag gagaggtgcg catggcgaag gcagggcggg aggggccgcg ggacagcgtg     60
tggctgtcgg gggaggggcg gcgcggcggt cgccgtgggg ggcagccgtc cgggctcgac    120
cgggaccgga tcaccggggt caccgtccgg ctgctggaca cggagggcct gacggggttc    180
tcgatgcgcc gcctggccgc cgagctgaac gtcaccgcga tgtccgtgta ctggtacgtc    240
gacaccaagg accagttgct cgagctcgcc ctggacgccg tcttcggcga gctgcgccac    300
ccggacccgg acgccgggct cgactggcgc gaggaactgc gggccctggc ccgggagaac    360
cgggcgctgc tggtgcgcca cccctggtcg tcccggctgg tcggcaccta cctcaacatc    420
ggcccgcact cgctggcctt ctcccgcgcg gtgcagaacg tcgtgcgccg cagcgggctg    480
cccgcgcacc gcctgaccgg cgccatctcg gccgtcttcc agttcgtcta cggctacggc    540
accatcgagg gccgcttcct cgcccgggtg gcggacaccg ggctgagtcc ggaggagtac    600
ttccaggact cgatgaccgc ggtgaccgag gtgccggaca ccgcgggcgt catcgaggac    660
gcgcaggaca tcatggcggc ccggggcggc gacaccgtgg cggagatgct ggaccgggac    720
ttcgagttcg ccctcgacct gctcgtcgcg ggcatcgacg cgatggtcga acaggcctga    780
```

<210> SEQ ID NO 30
<211> LENGTH: 66
<212> TYPE: DNA
<213> ORGANISM: Artificial Sequence
<220> FEATURE:
<223> OTHER INFORMATION: Primer

<400> SEQUENCE: 30

```
gtacgaattc gatatcatgc atggcgccgt ttaaacgcgt atttaaatga tccgctagcg     60
ctaccg                                                                66
```

-continued

<210> SEQ ID NO 31
<211> LENGTH: 135
<212> TYPE: DNA
<213> ORGANISM: Artificial Sequence
<220> FEATURE:
<223> OTHER INFORMATION: Primer

<400> SEQUENCE: 31

```
gatcaagctt gcggccgcgg atccgcccgg gccacacaaa aaaccaacac acagatgtaa      60
tgaaaataaa gatattttat tatcgatact agtgcgatcg cttaattaat ttaaatttac     120
ttgtacagct cgtcc                                                      135
```

ANTIBIOTIC-BASED GENE REGULATION SYSTEM

This application is a continuation-in-part of application Ser. No. 09/298,768, filed Apr. 23, 1999, now abandoned.

FIELD OF THE INVENTION

The invention relates to a novel system for gene regulation in eukaryotic cells, and methods of using the same for protein production. In particular, the invention provides a new system for antibiotic-regulated gene expression in eukaryotic cells based on sequences from Actinomycetes antibiotic resistance promoters, polypeptides that bind to the same in an antibiotic responsive manner, and nucleotides encoding such polypeptides.

BACKGROUND OF THE INVENTION

Controlled expression of transgenes or of target endogenous genes will likely be essential for success of many genetic therapies. Constitutive expression of transgenes has resulted in down-regulation of effector systems and/or cellular toxicity in animal studies (Efrat et al, 1995, Proc. Natl. Acad. Sci. USA 92, 3576–3580). Regulated expression in response to metabolic, hormonal, or environmental signals is the normal situation for many eukaryotic genes. In order to mimic natural physiological expression patterns with transgenes, and to minimize interactions with human gene regulation signals, binary promoter/transactivator configurations of heterologous origin which respond to heterologous stimuli have been developed in recent years. However, many exogenous stimuli which modulate these artificial mammalian regulons have proven to be incompatible with human therapeutic use due to cytotoxicity or undesired side effects (Baim et al., 1991, Proc. Natl. Acad. Sci. USA 88, 5072–5076; Braselmann et al., 1993, Proc. Natl. Acad. Sci. USA 90, 1657–1661; No D. et al., 1996, Proc. Natl. Acad. Sci. USA 93, 3346–3351; Rivera et al., 1996, Nat. Medicine 2, 1028–1032; Suhr et al., 1998, Proc. Natl. Acad. Sci. USA 95, 7999–8004; Wang et al., 1994, Proc. Natl. Acad. Sci. USA 91, 8180–8184). The tetracycline-regulated mammalian expression system avoids these problems, and is described in U.S. Pat. Nos. 5,888,981; 5,866,755; 5,789,156; 5,654,168; and 5,650,298, to name just a few examples. However, the tetracycline-regulated system can fail to suppress gene expression adequately under repressed conditions.

Moreover, future gene therapy strategies will require technology which allows independent control of two different transgenes or sets of transgenes which are cotranscribed in a multicistronic configuration. For example, many tissue expansion and ex vivo gene therapy scenarios will require a two-step process beginning with expression of growth-promoting genes to enable expansion of grafted tissues in culture, followed by induction of growth suppressors to prevent tumorigenic behavior of treated cells after reimplantation. Sustained proliferation control is also required for stem cell-based technologies currently evaluated for eventual cell and tissue replacement therapy, since stem cells are tumorigenic (Rossant et al., Nat. Biotechnol. 17, 23–24; Solter et al., Science 283, 1468–1470). The second independent gene regulation system could be used in such cells for pharmacologic control of one or several secreted therapeutic proteins, such as insulin, to enable titration of circulating proteins into the therapeutic range or adapt expression to optimal daily dosing regimes. There is, therefore, a need for new mammalian gene regulation systems which employ modern, therapeutically proven antibiotics as controlling agents, and which can be used in combination with the tetracycline regulation system, with minimal interaction between tetracycline control and the new control modality.

The human oral antibiotic pristinamycin consists, like other streptogramins, of a mixture of two structurally dissimilar molecules, the streptogramin A component pristinamycin II (PII), a polyunsaturated macrolactone, and the streptogramin B component pristinamycin I (PI), a cyclic hexadepsipeptide. The water-soluble form of pristinamycin, Synercid, recently approved in the U.S. and Europe for use against most multiple drug-resistant Gram-positive bacteria (Barriuere et al., 1994, Expert Opin. Invest. Drugs 3, 115–131; Baquero et al., 1997, J. Antimicrob. Chemother. 39, 1–6), is composed of dalfopristin, a 26-sulphonyl derivative of PII, and quinupristin, which is derived from PI by synthetic addition of a (5δ R)-[(3S)-quinuclidinyl] thiomethyl group. Virginiamycin is another important streptogramin used as a growth promotant in livestock feed (Nagaraja et al., 1998, J. Anim. Sci. 76, 287–298). Either the A or B streptogramin components are individually bacteriostatic, but streptogramins A and B together are synergistically bactericidal (up to 100 times more active), a phenomenon which lowers incidence of acquired antibiotic resistance, since high level resistance to the combined streptogramins is likely only when both type A and type B streptogramin resistance determinants are present simultaneously (Cocito et al, 1997, J. Antimicrob. Chemother. 39, 7–13). Recently, a pristinamycin resistance determinant (ptr) has been cloned from S. pristinaespiralis (Blanc et al., 1995, Mol. Microbiol. 17, 989–999; Salah-Bey et al., 1995, Mol. Microbiol. 17, 1001–1012; Salah-Bey et al., 1995, Mol. Microbiol. 17, 1109–1119). Expression from the ptr promoter (containing a recognition sequence termed $P_{PTR}$) is induced by pristinamycin, particularly by PI. A protein called Pip (pristinamycin-induced protein) was identified based on its affinity to $P_{PTR}$ in gel retardation experiments (Salah-Bey et al., 1995, Mol. Microbiol. 17, 1109–1119).

Recently, the prevalence of multidrug resistant human pathogenic bacteria has increased dramatically. This increase correlates with an escalation of bacterial disease and related mortality. Also, antibiotic chemotherapy is becoming more difficult as the percentage of elderly and immunocompromised patients grows. The European Commission has already reacted to this situation by banning the use of certain antibiotics as a growth promoter in livestock feed, among them the streptogramin virginiamycin, so as to limit the environmental spread of antibiotics (thought to be a major driving force for selection of multidrug resistant pathogenic bacteria) thereby preserving the use of antibiotics for human therapy.

SUMMARY OF THE INVENTION

The present invention is directed to a new system for antibiotic-regulated gene expression in eukaryotic cells based on sequences from Actinomycetes antibiotic resistance promoters, and polypeptides that bind to the same in an antibiotic responsive manner. In one aspect, the invention relates to an isolated nucleic acid encoding a polypeptide which binds to a $P_{abr}$ sequence in the absence of its cognate antibiotic. The $P_{abr}$ sequence is derived from an actinomycetes bacterium, in particular an antibiotic responsive operon from an actinomycetes bacterium. In another aspect, the invention relates to an isolated nucleic acid encoding a fusion protein which regulates transcription, the fusion protein having a first polypeptide which binds to a $P_{abr}$ sequence in the absence of its cognate antibiotic, operatively linked to a second polypeptide which activates or represses transcription in eukaryotic cells. In another aspect, the invention relates to the proteins encoded by such nucleic acids. These proteins can be used to activate or repress transcription from a desired nucleotide sequence to be transcribed that is operatively linked to a $P_{abr}$ sequence.

The invention also includes host cells that contain nucleic acids encoding the proteins and fusion proteins of the invention. Such host cells optionally contain a desired nucleotide sequence to be transcribed operatively linked to a $P_{abr}$ sequence. The nucleotide sequence to be transcribed can be endogenous or exogenous to the host cell.

Yet another aspect of the invention provides an isolated nucleic acid having a $P_{abr}$ sequence operatively linked to a first eukaryotic promoter. The first eukaryotic promoter can also be operatively linked to a first coding sequence. Optionally, the nucleic acid can also contain at least one tet operator sequence operatively linked to a second eukaryotic promoter, which in turn can be operatively linked to a second coding sequence. Either coding sequence can encode any protein of interest for which production is desired. Further, one of the coding sequences can encode a tumor suppressor gene product or a gene product which activates cell proliferation. Still further, at least one of the promoters can be operatively linked to more than one coding sequence through the use of, for example, an internal ribosomal entry site. Host cells genetically engineered to contain these nucleic acids are also provided by the invention. By "genetically engineered" is meant that the host cells are manipulated by molecular biology techniques, including transformation, transfection, and recombination (such as homologous or non-homologous recombination), to contain the desired nucleic acid. In another aspect, the invention provides a method for regulating expression of an $P_{abr}$-linked gene in a eukaryotic cell. The method entails introducing into the cell a nucleic acid molecule encoding a PIT. The PIT can be a $P_{abr}$-binding protein, or can comprise a $P_{abr}$-binding protein operably linked to a polypeptide that activates or represses transcription in eucaryotic cells, thereby rendering the $P_{abr}$-linked gene capable of regulation by an antibiotic that binds to the $P_{abr}$-binding protein in the cell. One can then modulate the level of the antibiotic in the cell to regulate expression of the $P_{abr}$-linked gene Still another aspect of the invention is a process for producing a protein by culturing a eukaryotic cell containing a $P_{abr}$-linked gene that encodes the protein and a nucleic acid molecule encoding a PIT. The PIT can be a $P_{abr}$-binding protein, or can comprise a $P_{abr}$-binding protein operably linked to a polypeptide that activates or represses transcription in eucaryotic cells. Expression of the $P_{abr}$-linked gene is then regulated by modulating the level of an antibiotic that binds to the $P_{abr}$-binding protein in the cell. Optionally, the process entails the step of collecting the protein produced by the cell.

Another aspect of the invention is a method of screening for candidate antibiotics. The method entails incubating the host cells of the invention, the host cells containing a $P_{abr}$-linked reporter gene and a sequence encoding a $P_{abr}$-binding protein, in the presence of a test compound, wherein a change in the transcription of the reporter gene indicates that the test compound is a candidate antibiotic.

BRIEF DESCRIPTION OF THE FIGURES

FIG. 9A illustrates vectors pTRIDENT9 and pTRIDENT10, while FIG. 9B illustrates pTRIDENT11 and pTRIDENT12. The pTRIDENT-derived mammalian expression vectors contain a tricistronic expression unit which is either driven by the pristinamycin-repressible ($P_{pir}$) or the pristinamycin-inducible ($P_{pir}$ON) promoter. Whereas the first cistron of the tricistronic expression unit is transcribed in a cap-dependent manner, the subsequent genes rely on cap-independent translation initiation based on internal ribosomal entry sites of polyioviral (IRES) origin or of encephalomyocarditis virus. The multicistronic expression unit is terminated by a polyadenylation site (pA) of the SV40 virus.

DETAILED DESCRIPTION OF THE INVENTION

Figure 1:
FIG. 1: Gel retardation assay showing Pip/$P_{PTR}$ interaction. $P_{PTR}$ of *S. pristinaespiralis* contains 3 dyad symmetrical binding sites (lane A; $P_{PTR}$ in the absence of Pip) all of which are saturated at relatively large amounts of purified Pip (0.4 pmol; lane A) resulting in a single shifted band. Smaller amounts of Pip (0.02 pmol) presented an intermediate situation in which all possible permutations of site occupancy are represented in three distinct retarded bands (lane C). Pip (0.2 pmol lanes D–M) was titrated with a range of PI from 50 pmol to 0.01 pmol (lanes D–H; D: 50 pmol; E: 10 pmol; F: 1 pmol; G: 0.1 pmol; H: 0.01 pmol). Under identical conditions the semisynthetic PI derivative quinupristin was also titrated (lanes I–M; 1: 50 pmol; J: 10 pmol; K: 1 pmol; L: 0.1 pmol; M: 0.01 pmol).

Systems to control expression of foreign genes will be essential tools for future cell- and gene-based human therapies. The present invention is directed to a new system for antibiotic-regulated gene expression in eukaryotic cells based on sequences from Actinomycetes antibiotic resistance promoters, and polypeptides that bind to the same in an antibiotic responsive manner.

For purposes of the invention, a $P_{abr}$ sequence is a sequence from an Actinomycetes antibiotic resistance promoter that binds a particular polypeptide, AIP (also referred to herein as a "polypeptide which binds to a $P_{abr}$ sequence in the absence of its cognate antibiotic"), in an antibiotic dependent way. The antibiotic resistance promoter can be derived from a naturally-occurring episome, but is preferably a chromosomal promoter. Preferably, AIP binds to the $P_{abr}$ sequence in the absence of its cognate antibiotic, and is released from the $P_{abr}$ sequence when antibiotic is present, although the reverse situation is also within the scope of the invention. Accordingly, in the presence of the AIP, expression from the antibiotic resistance promoter containing the $P_{abr}$ sequence is regulated by the presence or absence of antibiotic. Thus, for purposes of the invention, the term "cognate antibiotic" means the antibiotic which when bound to the AIP results in the release of the protein from its $P_{PIR}$ binding site.

AIPs are, for the purposes of the invention, derived from or related to AIP proteins produced by Actinomycetes. By "derived from" AIP proteins produced by Actinomycetes, is meant, in this context, that the amino acid sequence is identical to a naturally occurring AIP, or contains only conservative amino substitutions and but remains at least 70%, preferably 80%, and more preferably 90% identical at the amino acid level. By "related to" AIP proteins produced by Actinomycetes is meant, for purposes of the invention, that the polynucleotide sequence that encodes the amino acid sequence hybridizes to a naturally occurring AIP produced by Actinomycetes under at least low stringency conditions, more preferably moderate stringency conditions, and most preferably high stringency conditions, and binds to a $P_{abr}$ recognition sequence. Conservative substitutions known in the art and described by Dayhof, M. D., 1978, Nat. Biomed. Res. Found., Washington, D.C., Vol. 5, Sup. 3, among others. Genetically encoded amino acids are generally divided into four groups: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan and tyrosine are also jointly classified as aromatic amino acids. A substitution of one amino acid in a particular group with another amino acid in the same group is generally regarded as a conservative substitution. The Actinomycetes include Grain-positive bacteria from the following taxonomic groups: Actinomycineae; Corynebacterineae; Frankineae; Glycomycineae; Kineococcus group; Micrococcineae; Micromonosporineae; Propionibacterineae; Pseudonocardineae; Streptomycineae; Streptosporangineae; and unclassified Actinomycetales (Stackebrandt et al., 1997, Int. J. Syst. Bacteriol. 47 (2): 479–491). Additional information regarding Actinomycetes, and the members of each group, can be obtained from the National Center for Biotechnology taxonomy collection. Preferred actinomycetes are streptomycetes, and are thus from the group Streptomycineae.

The invention is illustrated below in one embodiment using a particularly preferred antibiotic system employing streptogramins and the Pip/$P_{PTR}$ interaction. Specifically, one particularly preferred AIB is the Pip of *S. coelicolor* binds to a particular $P_{abr}$, the $P_{PTR}$, recognition site in an antibiotic responsive manner. Thus the invention provides, in one aspect, the complete nucleotide coding sequence of the Pip protein (SEQ ID NO:29), and the deduced amino acid sequence of Pip. The amino acid sequence of Pip was used in protein database searches to identify additional Streptomyces and Amycolatopsis genes within antibiotic biosynthetic clusters bearing sequence similarity to Pip that may respond to other antibiotics. In particular, Pip contains a helix-turn-helix motif characteristic of DNA binding proteins. A computer search was conducted for proteins containing this motif encoded within antibiotic biosynthetic gene clusters which also encode a transmembrane protein antibiotic resistance gene. Results are shown the following Table 1. These actinomycetes, as well as others yet to be discovered or identified, can contain $P_{abr}$ sequences and AIPs that can be used in the compositions and methods of the invention.

TABLE 1

Sreptomyces and Amycolatopsis antibiotic biosynthetic gene clusters.

| Protein | % AA identity to Pip | Putative antibiotic inducer | Clinical approval | Actinomycete |
|---------|---------------------|------------------------------|-------------------|--------------|
| pip | 100 | pristinamycin I (confirmed) | + | *Streptomyces coelicolor* |
| rifQ | 49 | rifamycin | + | *Amycolatopsis mediterranei* (1) |
| orfY | <25 | rapamycin | + | *Streptomyces hygroscopicus* (5) |
| dnrO | <25 | daunorubicin (adriamycin) | + | *Streptomyces peucetius* (4) |
| actII (orf1) | 30 | actinorhodin | − | *Streptomyces coelicolor* (2) |
| tcmR | <25 | tetracenomycin (confirmed) | −(?) | *Streptomyces glaucescens* (3) |
| lanK | <25 | landomycin | −(?) | *Streptomyces cyanogenus* (6) |

References for TABLE 1 are as follows:
1. August et al., 1998, Biosynthesis of the ansamycin antibiotic rifamycin: deductions from the molecular analysis of the rif biosynthetic gene cluster of Amycolatopsis mediterranei S699. Chem. Biol. 5:69–79.
2. Fernandez et al., 1991, The act cluster contains regulatory and antibiotic export genes, direct targets for translational control by the bldA tRNA gene of Streptomyces. Cell 66:769–780.
3. Guilfoile et al., 1992, Sequence and transcriptional analysis of the Streptomyces glaucescens tcmAR tetracenomycin C resistance and repressor gene loci. J. Bacteriol 174:3651–8.
4. Otten et al., 1995, Regulation of daunorubicin production in *Streptomyces peucetius* by the dnrR2 locus. J. Bacteriol. 177:1216–1224.
5. Schwecke et al., 1995, The biosynthetic gene cluster for the polyketide immunosuppressant rapamycin. Proc Natl Acad Sci USA 92:7839–7843.
6. Westrich et al., 1999, Cloning and characterization of a gene cluster from *Streptomyces cyanogenus* S136 probably involved in landomycin biosynthesis. FEMS Microbiol Lett 170:381–7.

Actinomycetes antibiotic-resistant promoters that contain $P_{abr}$ sequences can also be identified by generating Actinomycetes gene libraries in a heterologous host, and growing the heterologous host under conditions containing selective antibiotics. Emerging resistant clones containing antibiotic resistant determinants can be identified by their characteristic protein binding motifs following sequence analysis.

Polynucleotide sequences encoding the first polypeptide which binds to a $P_{abr}$ sequence in the absence of its cognate antibiotic can be used to clone homologous AIPs in other actinomycetes. Such homologous AIPs can also be used as the first polypeptide of the fusion protein, and their $P_{abr}$ recognition sequence operably linked to the eukaryotic promoter of interest. Thus, the invention also relates to nucleic acids hybridizable to or complementary to nucleotides which encode the AIPs described herein. A preferred AIP is the repressor of a streptogramin resistance operon of S. coelicolor, Pip, described more fully below. Such AIPs are at least 50%, preferably 60%, more preferably 70%, even more preferably 80%, yet more preferably 90%, and most preferably 95% homologous at the amino acid sequence level to an AIP described herein Homology can be calculated using, for example, the BLAST computer program, version 2.0, available on the World-Wide Web. Typical parameters for determining the similarity of two sequences using BLAST 2.0 are a reward for match of 1, penalty for mismatch of −2, open gap and extension gap penalties of 5 and 2, respectively, a gap dropoff of 50, and a word size of 11.

In a specific embodiment, a nucleic acid that is hybridizable to an AIP nucleic acid, or to a nucleic acid encoding an AIP amino acid, under conditions of low stringency is provided. Procedures using such conditions of low stringency are as follows (see also Shilo and Weinberg, 1981, Proc. Natl. Acad. Sci. USA 78:6789–6792): Filters containing DNA are pretreated for 6 h at 40° C. in a solution containing 35% formamide, 5X SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2X SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and reexposed to film. Other conditions of low stringency which can be used are well known in the art (e.g., as employed for cross-species hybridizations).

In another specific embodiment, a nucleic acid that is hybridizable to an AIP nucleic acid, or to a nucleic acid encoding an AIP amino acid, under conditions of moderate stringency is provided. Procedures using such conditions of moderate stringency are as follows: Filters containing DNA are pretreated for 6 h at 55° C. in a solution containing 6X SSC, 5X Denhart's solution, 0.5% SDS and 100 µg/ml denatured salmon sperm DNA. Hybridizations are carried out in the same solution and 5–20×10$^6$ cpm $^{32}$P-labeled probe is used. Filters are incubated in hybridization mixture for 18–20 h at 55° C., and then washed twice for 30 minutes at 60° C. in a solution containing 1X SSC and 0.1% SDS. Filters are blotted dry and exposed for autoradiography. Other conditions of moderate stringency which can be used are well-known in the art. Washing of filters is done at 37° C. for 1 h in a solution containing 2X SSC, 0.1% SDS.

In another specific embodiment, a nucleic acid that is hybridizable to an AIP nucleic acid, or to a nucleic acid encoding an AIP amino acid, under conditions of high stringency is provided. Procedures using such conditions of high stringency are as follows: Prehybridization of filters containing DNA is carried out for 8 h to overnight at 65° C. in buffer composed of 6X SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10$^6$ cpm of $^{32}$P-labeled probe. Washing of filters is done at 37° C. for 1 h in a solution containing 2X SSC, 0.01% PVP, 0.01% Ficoll, and 0.01% BSA. This is followed by a wash in 0.1X SSC at 50° C. for 45 min before autoradiography. Other conditions of high stringency which can be used are well known in the art.

New AIP proteins can also be isolated by binding to $P_{abr}$ sequences. For example, the polynucleotide with the $P_{abr}$ sequence is immobilized on a matrix and ideally packed in a column. Bacterial extracts are applied to the column under conditions which allow PIP homologs to bind to the immobilized target sequence. Following appropriate washing steps, the PIP homolog is eluted by suitable conditions (e.g., addition of antibiotic) and the sequence of the purified protein determined and the corresponding gene cloned.

The invention also includes isolated or purified AIP proteins and polypeptides of the invention. AIP proteins of the invention include polypeptides that bind to $P_{abr}$ sequences, as well as fusion proteins containing a first polypeptide that binds to $P_{abr}$ sequences operatively linked to a second polypeptide which activates or represses transcription in eukaryotic cells. In this context, operatively linked means that the two proteins are covalently or non-covalently bound to one another in such a manner that they retain their functional activities of binding to $P_{abr}$ sequence (first polypeptide) and activating or repressing transcription (second polypeptide).

As used herein, a polypeptide is "substantially purified" where the polypeptide constitutes the majority (i.e., at least about 50%) by weight of the material in a particular preparation. Also, as used herein, a polypeptide is "isolated" where the polypeptide constitutes at least about 90 wt % of the material in a particular preparation.

The fusion proteins of the invention contain both the first polypeptide which binds to a $P_{abr}$ sequence in the absence of its cognate antibiotic, and a second polypeptide which activates or represses transcription in eukaryotic cells. By activating transcription is meant that the rate of transcriptional initiation is increased from the nucleotide sequence to be transcribed that is operatively linked to a $P_{abr}$ sequence when the fusion protein that activates transcription is bound to the $P_{abr}$ sequence, as opposed to when it is not bound. Similarly, by repression of transcription is meant that the rate of transcriptional initiation is decreased from the nucleotide sequence to be transcribed that is operatively linked to a $P_{abr}$ sequence when the fusion protein that represses transcription is bound to the $P_{abr}$ sequence, as opposed to when it not bound.

Accordingly, in one aspect, the first polypeptide of the fusion protein that activates transcription is operatively linked to a second polypeptide which directly or indirectly activates transcription in eukaryotic cells. To operatively link the first and second polypeptides, typically nucleotide sequences encoding the first and second polypeptides are ligated to each other in-frame to create a chimeric gene encoding a fusion protein, although the first and second polypeptides can be operatively linked by other means that preserve the function of each polypeptide (e.g., chemically crosslinked). The first and second polypeptides can be in any order. The second polypeptide of the transactivator can itself possess transcriptional activation activity (i.e., the second polypeptide directly activates transcription) or it activates transcription by an indirect mechanism, through recruitment of a transcriptional activation protein to interact with the fusion protein. Accordingly, the term "a polypeptide which activates transcription in eukaryotic cells" includes polypeptides which either directly or indirectly activate transcription.

Polypeptides which can function to activate transcription in eukaryotic cells are well known in the art and are described, for example, in U.S. Pat. No. 5,654,168. Such polypeptides include the herpes simplex virus virion protein 16 (VP16, the amino acid sequence of which is disclosed in Triezenberg, S. J. et al., 1988, Genes Dev. 2:718–729), particularly the 127 amino acid C-terminus or the 11 amino acid C-terminus. Suitable C-terminal peptide portions of VP16 are described in Seipel, K. et al. (EMBO J., 1992, 13:4961–4968).

Acidic transcription activation domains, proline-rich transcription activation domains, serine/threonine-rich transcription activation domains and glutamine-rich transcription activation domains can all be used in the compositions and methods of the invention. VP16 polypeptides and amino acid residues 753–881 of GAL4 are acidic activating domains. Another polypeptide that activates transcription is the p65 domain of NF-κB (Schmitz and Baeuerle, 1991, EMBO J. 10:3805–3817). Examples of proline-rich activation domains include amino acid residues 399–499 of CTF/NF1 and amino acid residues 31–76 of AP2. Examples of serine/threonine-rich transcription activation domains include amino acid residues 1–427 of ITF1 and amino acid residues 2–451 of ITF2. Examples of glutamine-rich activation domains include amino acid residues 175–269 of Oct1 and amino acid residues 132–243 of Sp1. The amino acid sequences of each of the above described regions, and of other useful transcriptional activation domains, are disclosed in Seipel, K. et al. (EMBO J., 1992, 13:4961–4968). This reference also describes methods of identifying new transcriptional activation domains which are within the scope of the invention.

In another embodiment, the second polypeptide of the fusion protein indirectly activates transcription by forming a non-covalent association with a transcriptional activator. For example, an AIP of the invention can be fused to a polypeptide domain (e.g., a dimerization domain) capable of mediating a protein-protein interaction with a transcriptional activator protein, such as an endogenous activator present in a host cell. Non-covalent interactions between DNA binding domains and transactivation domains are known in the art (see e.g., Fields and Song, 1989, Nature 340:245–247; Chien et al., 1991, Proc. Natl. Acad Sci. USA 88:9578–9582; Gyuris et al., 1993, Cell 75:791–803; and Zervos, A. S., 1993, Cell 72:223–232). Examples of suitable interaction (or dimerization) domains include leucine zippers (Landschulz et al., 1989, Science 243:1681–1688), helix-loop-helix domains (Murre, C. et al., 1989, Cell 58:537–544) and zinc finger domains (Frankel, A. D. et al., 1988, Science 240:70–73).

In another aspect, the polypeptide that binds $P_{abr}$ can be used by itself to repress transcription in the absence of antibiotic. In this manner, the polypeptide that binds $P_{abr}$ prevents transcription when bound to the $P_{abr}$ sequence, presumably by interfering with binding of activating transcription factors. In the absence of antibiotic, transcription from the $P_{abr}$ linked promoter is absent or minimal. When antibiotic is added, however, the polypeptide that binds $P_{abr}$ is released, thereby allowing transcription to occur.

In an alternative embodiment, the fusion protein that binds $P_{abr}$ can be used to repress transcription. In one aspect, the first polypeptide is operatively linked, as described above, to a second polypeptide which directly or indirectly represses transcription in eukaryotic cells. Proteins and polypeptide domains within proteins which can function to repress transcription in eukaryotic cells have been described in the art (for reviews see, e.g., Renkawitz, R., 1990, Trends in Genetics 6:192–197; and Herschbach, B. M. and Johnson, A. D., 1993, Annu. Rev. Cell. Biol. 9:479–509). Such domain can have a direct inhibitory effect on the transcriptional machinery or can repress transcription indirectly by inhibiting the activity of activator proteins. Accordingly, the term "a polypeptide that represses transcription in eukaryotic cells" as used herein is intended to include polypeptides which act either directly or indirectly to repress transcription. As used herein, "repression" of transcription is intended to mean a diminution in the level or amount of transcription of a target gene compared to the level or amount of transcription prior to regulation by the transcriptional inhibitor protein. Transcriptional inhibition may be partial or complete.

A transcriptional "repressor" or "silencer" domain as described herein is a polypeptide domain that retains its ability to repress transcription when the domain is transferred to a heterologous protein. Proteins which have been demonstrated to have repressor domains that can function when transferred to a heterologous protein include the v-erbA oncogene product (Baniahinad, A. et al., 1992, EMBO J. 11:1015–1023) (e.g., approximately amino acid residues 362–632 of the native v-erbA oncogene product), the thyroid hormone receptor (Baniahmad, supra), the retinoic acid receptor (Baniahmad, supra), the Drosophila Krueppel (Kr) protein (Licht, J. D. et al., 1990, Nature 346:76–79; Sauer, F. and Jackle, H., 1991, Nature 353:563–566; Licht, J. D. et al., 1994, Mol. Cell. Biol. 14:4057–4066) (such as C64KR, which is amino acids 403–466 of the native protein, or amino acids 26–110 of Kr), and the KRAB domain of the kox1 gene family (Deuschle et al., 1995, Mol. Cell. Biol. 15:1907–1914). Other proteins which have transcriptional repressor activity in eukaryotic cells include the Drosophila homeodomain protein even-skipped (eve) (Han and Manley, 1993, Genes & Dev. 7: 491–503), the S. cerevisiae Ssn6/Tup1 protein complex (Herschbach and Johnson, supra), the yeast SIRI protein (see Chien et al., 1993, Cell 75:531–541), NeP1 (see Kohne et al., 1993, J Mol. Biol. 232:747–755), the Drosophila dorsal protein (see Kirov et al., 1994, Mol. Cell. Biol. 14:713–722; Jiang, et al., 1993, EMBO J. 12:3201–3209), TSF3 (see Chen, et al., 1993, Mol. Cell. Biol. 13:831–840), SF1 (see Targa, et al., 1992, Biochem. Biophys. Res. Comm. 188:416–423), the Drosophila hunchback protein (see Zhang, et al., 1992, Proc. Natl. Acad. Sci. USA 89:7511–7515), the Drosophila knirps protein (see Gerwin, et al., 1994, Mol. Cell. Biol. 14:7899–7908), the WT1 protein (Wilm's tumor gene product) (see Anant, et al., 1994, Oncogene 9:3113–3126; Madden et al., 1993, Oncogene 8:1713–1720), Oct-2.1 (see Lillycrop, et al., 1994, Mol. Cell. Biol. 14:7633–7642), the Drosophila engrailed protein (see Badiani, et al., 1994, Genes Dev. 8:770–782; Han and Manley, 1993, EMBO J. 12:2723–2733), E4BP4 (see Cowell and Hurst, 1994, Nucleic Acids Res. 22:59–65) and ZF5 (see Numoto, et al., 1993, Nucleic Acids Res. 21:3767–3775).

Non-limiting examples of polypeptide domains that can be used as silencing domains include: amino acid residues 120–410 of the thyroid hormone receptor alpha (THR.alpha.), amino acid residues 143–403 of the retinoic acid receptor alpha (RAR.alpha.), amino acid residues 186–232 of knirps, the N-terminal region of WT 1 (see Anant, supra), the N-terminal region of Oct-2.1 (see Lillycrop, supra), a 65 amino acid domain of E4BP4 (see Cowell and Hurst, supra) and the N-terminal zinc finger domain of ZF5 (see Numoto, supra). Moreover, shorter or longer polypeptide fragments encompassing these regions that still retain full or partial repression activity are also contemplated.

In addition to previously described transcriptional repressor domains, novel transcriptional repressor domains, which can be identified by standard techniques (e.g., reporter gene constructs), are within the scope of the invention.

Construction of the nucleic acids of the invention can be accomplished by those of skill in the art using standard molecular biology techniques (see, for example, Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.). Typically, manipulation and generation of nucleic acids is performed using prokaryotic host cells, but the invention also encompasses chemical synthetic methods of nucleic acid generation and manipulation.

The host cells for use in the methods and compositions of the invention can also be any eukaryotic cell such as mammalian cells, fungal cells, plant cells and microbial parasites. The invention is illustrating below by way of non-limiting examples using a variety of mammalian cells. However, other types of eukaryotic cells can also be used. For example, the tetracycline-regulatable promoter system has been adapted for use in yeast (Gari et al., 1997, Yeast 13:837–848); similarly, the methods and compositions of the invention can also be used in such cells. Methods of genetically engineering a host cell to contain the nucleic acids of the invention are well known to those of skill in the art and include transformation, transfection, and electroporation. The nucleic acids can be carried extrachromasomally or on the chromosome. Integration can be random, homologous, or site-specific recombination. Culturing a host cell is understood to include both in vitro culture and in vivo culture (for example, growing eukaryotic cells in tissue culture, growing cells in a host organism such as by implantation in a body cavity or graft, removing cells from a particular individual and replacing them after genetically engineering the cells to contain the nucleic acids of the invention, etc.).

A $P_{abr}$-linked gene is defined herein as a promoter which directs the expression of a coding sequence, wherein the promoter and coding sequence are operatively linked to a $P_{abr}$ sequence. Preferably, the promoter is a eukaryotic promoter. By operatively linked in this context is meant that the $P_{abr}$ sequence is placed proximal to the promoter, either 5' to, or 3' to, or within the sequence of the promoter, such that when a fusion protein that modulates transcription is bound to the $P_{abr}$ sequence, initiation of transcription at the promoter is affected. Particularly preferred $P_{abr}$ sequences are those $P_{abr}$ sequences from S. coelicolor and S. pristinaespiralis; the use of these sequences to construct $P_{abr}$-linked genes are illustrated below by way of non-limiting examples.

The coding sequence operatively linked to the promoter can encode for any gene product for which regulated expression is desired, and can be exogenous to the host cell or endogenous. By endogenous coding sequence is meant coding sequence that is naturally present in the host cell and not introduced into the host cell via transformation techniques. Exogenous coding sequence is not endogenous coding sequence. Coding sequences include not only sequences encoding proteins, but also other coding sequences, e.g., encoding antisense gene products, ribozymes, etc. Further, the coding sequences can be multicistronic (see, for example, U.S. application Ser. No. 08/948,381, filed Oct. 9, 1997).

Production of any gene product can be regulated using the compositions and methods of the present invention. For example, production of a marker gene product, such as green fluorescent protein, or of a model secreted gene product, such as SEAP, may be regulated. Naturally, the invention finds particular use in the production of products of industrial or pharmaceutical interest such as industrial enzymes (e.g. proteases, cellulases, glycosidases, or ligninases), interferons (e.g. β-INF, α-INF, γ-INF), hGH, insulin, erythropoietin, tissue plasminogen activator (tPA), DNAse, monoclonal antibodies, Factor VIII, Factor VII, Factor IX, HSA, IL-2, glucagon, EGF, GCSF, GMCSF, thrombopoietin, gp160, HbSAg, and other viral antigenic proteins and peptides (rotavirus, HIV, p53ras).

Another aspect of the invention is the use of tumor suppressor gene products to regulate proliferation of the host cells of the invention. Regulated expression of tumor suppressor gene products are particularly useful for a variety of applications. For example, one may want the host cells to undergo a rapid proliferation phase followed by a production phase where cellular energies are devoted to protein production, or a rapid proliferation phase in vitro followed by regulated growth in vivo (see, for example, U.S. application Ser. No. 08/948,381, filed Oct. 9, 1997, the disclosure of which is incorporated by reference). For purposes of the invention, tumor suppressor gene products are intracellular proteins that block the cell cycle at a cell cycle checkpoint by interaction with cyclins, Cdks or cyclin-Cdk complexes, or by induction of proteins that do so. Thus, these tumor suppressor gene products inhibit the cyclin-dependent progression of the cell cycle. Particularly preferred tumor suppressor gene products act on the G1-S transition of the cell cycle. The invention encompasses the use of any tumor suppressor gene product which performs this function, whether known or yet to be discovered. Examples of tumor suppressor genes include p21, p27, p53 (and particularly, the p53175P mutant allele), p57, p15, p16, p18, p19, p73, GADD45 and APC1.

Optionally, one can also use the methods and compositions of the invention to express survival factors in the host cells. Survival factors are intracellular proteins that prevent apoptosis such as bcl-2, bcl-$x_L$, E1B-19K, mcl-1, cimA, ab1, p35, bag-1, A20, LMP-1, Tax, Ras, Rel and NF-κB-like factors. Additionally, all known survival factors, as well as survival factors yet to be discovered, are useful in the methods and compositions of the invention. In yet another embodiment, the tumor suppressor gene(s) is expressed concomitantly with a factor that stabilizes the tumor suppressor gene product in the cell. Examples of stabilizing factors are members of the CAAT enhancer binding protein family. For example, p21 protein activity is stabilized when coexpressed with C/EBPα. Additionally, C/EBPα specifically induces transcription of the endogenous p21 gene. Thus, C/EBPα functions as both a stabilizing factor and as a specific inducer of p21.

Still another aspect of the invention is the use of a nucleotides and methods of the invention to express a gene product that activates cell proliferation. For example, a protein that activates cell proliferation is Mek1, a central protein kinase in the conserved mammalian Ras-MAP signal transduction pathway responding to growth-promoting signals such as cytokines. A particularly preferred version of Mek1 is the Mek1 DD mutant (Gruelich and Erikson, 1998, J. Biol. Chem. 273: 13280–13288) described more fully below. Other genetic determinants exerting positive control of mammalian cell cycle that can be used as a protein that activates cell proliferation are cyclins (e.g., cyclin E), Ras, Raf, the MAP kinase family (e.g., MAP, Erk, Sap) E2F, Src, Jak, Jun, Fos, pRB, Mek2, EGF, TGF, PDGF, and a polynucleotide that is antisense to a tumor suppressor gene (e.g., p27 antisense expression has been shown to stimulate proliferation of quiescent fibroblasts and enable growth in serun-free medium (Rivard et al., 1996, J. Biol. Chem. 271: 18337–18341.) and nedd5 which is known as positive growth controlling gene (Kinoshita et al, 1997, Genes Dev. 11: 1535–1547).

One aspect of the present invention is illustrated below by the development of a new system for antibiotic-regulated gene expression in eukaryotic cells based on the repressor of a streptogramin resistance operon of S. coelicolor (a Pip). A Pip protein (PIT4), or chimeric Pip proteins (PIT and PIT2) fused to a eukaryotic transactivator were able to control expression of a synthetic eukaryotic promoter ($P_{PIR}$) containing the $P_{ptr}$-binding site (in other words, a $P_{abr}$-linked gene). Genes placed under the control of this PIT/$P_{PIR}$ system were responsive to clinically approved therapeutic compounds belonging to the streptogramin group (pristinamycin, virginiamycin and Synercid) in a variety of mammalian cell lines (CHO-K1, BHK-21 and HeLa). This novel system exhibited superior inducibility and background expression properties compared to the well-established tetracycline-based system in CHO cells engineered to provide both streptogramin and tetracycline regulation. In these cells, streptogramin does not affect gene expression from the tetracycline-responsive promoter, and therapeutically relevant tetracycline concentrations have only minor effect on expression from the streptogramin-responsive PIT/$P_{PIR}$ system. Therefore, these two different systems can be used together in advanced therapies requiring independent regulation of different transgenes. In addition, responsiveness of the PIT/$P_{PIR}$ system to all type B streptogramins tested indicates that reporter gene expression from $P_{PIR}$ can be used as an efficient high-throughput assay for discovery of new streptogramins. The same concept applies to other eukaryotic antibiotic-responsive transcription regulation systems which can be linked to a reporter gene for the discovery of new antibiotics.

Another aspect of the invention is the development of a double-regulation system particularly advantageous when independent control of at least two different transgenes or sets of transgenes is desired. For example, this aspect of the invention is illustrated by way of a non-limiting example using the combined installation of tetracycline-dependent and pristinamycin-responsive gene regulation in the same cells. In the examples below, a double regulation vector pDuoRex1 was constructed which contains both tetracycline-dependent and pristinamycin-responsive expression units. These units were used, for example, to express the tumor suppressor gene p27 (under the control of the tetracycline-responsive promoter) and a gene product stimulating cell proliferation such as Mek1 (here under the control of $P_{PIR}$) (pMF195). For advanced gene therapy and tissue engineering strategies, induction of Mek1 (while repressing p27) can activate proliferation of grafted cells and facilitate cell expression while induction of p27 (while repressing Mek1) will arrest cell proliferation which is a desired trait for reimplantation of engineered cells and tissues. Other tumor suppressor genes and other genes stimulating cell proliferation can be substituted.

Still another aspect of the invention are multipurpose expression vectors, as well as cells and methods using the same, which take advantage of the antibiotic dependent activator and repressor systems of the invention. Such vectors can be mono, di- or multicitronic. Non-limiting examples of such vectors are described below by way of working embodiments.

Although the regulated gene expression invention described herein was originally designed for general applications in functional genomic research, gene therapy and tissue engineering, the finding that the streptogramin system illustrated below by way of nonlimiting example responds to all commercially available streptogramins, including Synercid, Pyostacin, and virginiamycin, indicates its use as a powerful screening tool for the discovery of novel antibiotics. Accordingly, still another aspect of the invention is a method of screening for candidate antibiotics. The method entails incubating host cells of the invention, the host cells containing a $P_{abr}$-linked reporter gene and a sequence encoding a $P_{abr}$-binding protein, in the presence of a test compound, wherein a change in the transcription of the reporter gene indicates that the test compound is a candidate antibiotic.

For example and not by way of limitation, detection of streptogramins is based on addition of metabolic libraries of Streptomyces or fungal origin to cultured mammalian cells containing the pristinamycin-responsive reporter system. The presence of streptogramins will downregulate expression of the reporter protein, for example SEAP, driven by $P_{PIR}$. This screening approach offers two decisive advantages over classical screening technology using indicator bacteria-based antibiogram tests: (i) Antibiotic screening is not limited by the sensitivity of indicator bacteria to a yet uncharacterized streptogramin (sensitivity of bacteria to antibiotics greatly varies between strains and even isolates), and (ii) the mammalian cell-based streptogramin detection concept shows at least one order of magnitude higher sensitivity to this class of antibiotics than antibiogram tests based on bactericidal activity. However, given the suggested interaction of Pip with other classes of antibiotics (a list is given in Salah-Bey K, Blanc, V., and Thompson C. J, 1995; Mol. Microbiol. 17, 1001–1012) the Pip/$P_{PIR}$-based mammalian gene regulation system can detect other antibiotic compounds. Also, extension of this detection concept to include antibiotic-responsive reporter gene expression using other AIP and $P_{abr}$ components from other Actinomycetes is within the scope of this invention.

The invention having been described, the following examples are offered by way of illustration and not limitation.

EXAMPLE 1
Steptogramin-Repressible Mammalian Gene Regulation System

After showing that the presence of PI reverses Pip association with $P_{PTR}$ in vitro, this example describes the use of Pip and $P_{PTR}$ to design a novel streptogramin-responsive mammalian gene regulation system with excellent regulatory properties which is functionally compatible with the tetracycline-based transcription regulation system (TET system) most widely used presently.

METHODS
Construction of the streptogramin-dependent transactivator (PIT) and the pristinamycin-regulatable promoter $P_{PIR}$ PIT, the fusion protein of Pip and the VP16 C-terminal transactivation domain of *Herpes simplex* (Triezenberg et al., 1988, Genes Dev. 2, 718–729) was constructed by amplifying the *S. coelicolor* Pip from pGemT::Epip4 with oligos:

OMF63: GTACGAATTCCCACCATGAGTCGAG-GAGAGGTG (SEQ ID NO:1) and

OMF64: GCGCGCGGCTGTACGCGGAGGCCTGTTC-GACCATC (SEQ ID NO:2) followed by cloning into vector pcDNA3.1/V5/His-TOPO (Invitrogen) under control of $P_{CMV}$ (PMF150). These primers can also be used to clone the desired gene sequences from *S. pristinaespiralis* genomic DNA.

$P_{PIR}$ seqence (SEQ ID NO:3):
GATCGACGTCGGAGAAATAGCGCTGTA-CAGCGTATGGGAATCTCTTGTACGGTGTACGAGT ATCTTCCCGTACACCGTACAAGGAGCCT-GCAGGgagtaccctcgaccgCcgGAGTATAAAT AGAG-GCGCTTCGTCTACGGAGCGACAAT-TCAATTCAAACAAGCAAAGTGAACACGTCGCTA AGCGAAAGCTAAGCAAATAAACAAGCG-CAGCTGAACAAGCTAAACAATCTGCAG-TAAAGTG CAAGTTAAAGTGAATCAATTAAAAG-TAACCAGCAACCAAGTAAATCAACTGCAACTA CTGA AATCTGCCAAGAAGTAATTATTGAATA-CAAGAAGAGAACTCTGAATACTTTCAA-CAAGTTA CCGAGAAAGAAGAACTCACACA-CAGCTAGCGTTTAAACTTAAGCTTGGTACCGAG CTCGGA TCCACTAGTCCAGTGTGGTGGAATTC.

The Pip-containing SspI/BssHII fragment of pMF150 was subsequently cloned into the corresponding sites of pSBC2-tTA (pSAM200 (SspI/BssHII) (Fussenegger et al., 1997, Biotechnol. Prog. 13, 733–740) thereby replacing the TetR Domain of tTA by Pip. The resulting plasmid has the following PIT coding sequence:

PIT sequence (SEQ ID NO:4):
ATGAGTCGAGGAGAGGTGCGCATGGC-GAAGGCAGGGCGGGAGGGGCCGCGGGA-CAGCGTGT GGCTGTCGGGGAGGGGCGGCGCG-GCGGTCGCCGTGGGGGGCAGCCGTCCGGGCT CGACCG GGACCGGATCACCGGGGTCACCGTC-CGGCTGCTGGACACGGAGGGCCT-GACGGGGTTCTCG ATGCGCCGCCTGGCCG CCGAGCTGAACGTCACCGCGATGTCCGT-GTACTGGTACGTCACA CCAAGGACCAGT-TGCTCGAGCTCGCCCTGGACGCCGTCT-TCGGCGAGCTGCGCCACCCGGA CCCGGACGCCGGGCTCGACTGGCGCGAG-GAACTGCGGGCCCTGGCCCGGGAGAACCGGGCG CTGCTGGTGCGCCACCCCTGGTCGTC-CCGGCTGGTCGGCACCTACCTCAA-CATCGGCCCGC ACTCGCTGGCCTTCT CCCGCGCGGTGCAGAACGTCGTGCGCCG-CAGCGGGCTGCCCGCGCA CCGCCTGACCG-GCGCCATCTCGGCCGTCTTCCAGT-TCGTCTACGGCTACGGCACCATCGAG GGCCGCTTCCTCGCCCGGGT GGCGGACAC-CGGGCTGAGTCCGGAGGAGTACTTCCAGGACT CGATGACCGCGGTGACCGAGGTGCCGGA-CACCGCGGGCGTCATCGAGGACGCGCAGGACAT CATGGCGGCCCGGGGCGGCGACACCGTG-GCGGAGATGCTGGACCGGGACTTCGAGTTCGCC CTCGACCTGCTCGTCGCGGGCATC-GACGCGATGGTCGAACAGGCCTCCGCG-TACAGCCGCG CGCGTACGAAAAACAAT-TACGGGTCTACCATCGAGGGCCTGCTCGATCT CCCGGACGACGA CGCCCCCGAAGAG-GCGGGGCTGGCGGCTCCGCGCCTGTC-CTTTCTCCCCGCGGGACACACG CGCAGACTGTC-GACGGCCCCCCCGACCGATGTCAGCCTGGG GGACGAG CTCCACTTAGACG GCGAGGACGTG-GCGATGGCGCATGCCGACGCGCTAGAC-GATTTCGATCTGGACATGTTGGG GGACGGGGAT-TCCCCGGGTCC GGGATTTACCCCCCACGACTCCGC-CCCCTACGGCGCTCTG GATATGGCCGACTTC-GAGTTTGAGCAGATGTTTACCGATGC-CCTTGGAATTGACGAGTACG GTGGGTAG PIT2, the fusion protein of Pip and the p65 transactivation domain of the human NF-κB transcription activator was cloned in a three step procedure: (i) The p65 domain of the human NF-κB transcription activator was amplified from pSG424-p65 (kindly provided by H. Hauser, GBF, Braunschweig, Germany) with oligos OMF97:

GATCGCGCGCATGATGAGTTTCCCACC (SEQ ID NO:22) and OMF98:

GATCAAGCTTGGATCCTTAGGAGCTGATCTGACT (SEQ ID NO:23) and cloned in sense orientation into pcDNA3.1/V5/His-TOPO (Invitrogen) to result in plasmid pMF197. (ii) pMF197 was restricted with BssHII and HindIII contained in the oligos (underlined) and the p65 domain was ligated to the corresponding sites (BssHII/HindIII) of pSBC2-tTA (Fussenegger et al., 1997) thereby replacing the VP16 domain of the tetracycline-dependent transactivator and resulting in plasmid pMF204. (iii) The tetR domain was excised from pMF204 by SspI/BssHII and replaced by Pip excised from pMF150 by SspI/BssHII to give plasmid pMF206. pMF206 contains the following PIT2 coding sequence:

ATGAGTCGAGGAGAGGTGCGCATGGC-GAAGGCAGGGCGGGAGGGGCCGCGGGA-CAGCGTGT GGCTGTCGGGGAGGGGCGGCGCG-GCGGTCGCCGTGGGGGGCAGCCGTCCGGGC TCGACCG GGACCGGATCACCGGGGTCACCGTC-CGGCTGCTGGACACGGAGGGCCT-GACGGGGTTCTCG ATGCGCCGCCTGGCCGC-CGAGCTGAACGTCACCGCGATGTCCGTGTACT GGTACGTCGACA CCAAGGACCAGTTGCTC-GAGCTCGCCCTGGACGCCGTCTTCGGC-GAGCTGCGCCACCCGGA CCCGGACGC-CGGGCTCGACTGGCGCGAGGAACTGCGGGCCC TGGCCCGGGAGAACCGGGCG CTGCTGGTGCGC-CACCCCTGGTCGTCCCGGCTGGTCG-GCACCTACCTCAACATCGGCCCGC ACTCGCTG-GCCTTC TCCCGCGCGGTGCAGAACGTCGTGCGC-CGCAGCGGGCTGCCCGCGCA CCGCCTGACCG-GCGCCATCTCGGCCGTCTTCCAGT-TCGTCTACGGCTACGGCACCATCGAG GGCCGCTTCCTCGCCCGGGTGGCGGA-CACCGGGCTGAGTCCGGAGGAGTACTTC-CAGGACT CGATGACCGCGGTGACCGAGGT GCCGGACACCGCGGGCGTCATCGAG-GACGCGCAGGACAT CATGGCGGCCCGGGGCG-GCGACACCGTGGCGGAGATGCTGGAC-CGGGACTTCGAGTTCGCC CTCGACCTGCTCGTCGCGGGCATC-GACGCGATGGTCGAACAGGCCTCCGCG-TACAGCCGCG CGCATGATGAGTTTCCCACCATG-GTGTTTCCTTCTGGGCAGATCAGCCAGGCCT CGGCCTT GGCCCCGGCCCTCCCCAAGTCCTGC-CCCAGGCTCCAGCCCCTGCCCCTGCTC-CAGCCATG GTATCAGCTCTGGCCCAG GCCCCAGCCCCTGTCCCAGTCCTAGC-CCCAGGCCCTCCTCAGG CTGTGGCCCCACCTGC-CCCCAAGCCCACCCAGGCTGGGGAAG-GAACGCTGTCAGAGGCCCT GCTGCAGCTGCAGTTTGATGATGAAGAC-CTGGGGGCCTTGCTTGGCAACAGCACAGACCCA GCTGTGTTCACAGACCTGGCATCCGTC-GACAACTCCGAGTTTCAGCAGCTGCT-

GAACCAGG GCATACCTGTGGCCCCCACA-
CAACTGAGCCCATGCTGATGGAGTACCCTGA
GGCTATAAC TCGCCTAGTGACAGGGGCCCAGAG-
GCCCCCCGACCCAGCTCCTGCTC-
CACTGGGGGCCCCG GGGCTCCCCAATGGCCTC-
CTTTCAGGAGATGAAGACTTCTCCTCCATTGC
GGACATGGACT TCTCAGCCCTGCTGAGTCAGAT-
CAGCTCCTAA (SEQ ID NO:24).

For construction of $P_{PIR}$ the minimal promoter of the Drosophila heat-shock gene hsp70 $P_{hsp70min}$; bp-40 to 241; Corces et al., 1984, J. Biol. Chem. 259, 14812–14817) contained on pTRIDENT7 (Fussenegger et al., 1998, Biotechnol. Bioeng. 57, 1–10) was amplified by PCR using oligos
OMF62:CTTGTACGGTGTACGAGTATCTTCCCGTA
CACCGTACAAGGAGCCTGCAGGgagt accctcgac-
cgccg (SEQ ID NO:5) and OMF57: GATCCATCGAT-
TGATCAGGCGC (SEQ ID NO:6) and cloned in anti-
lacZ orientation into the pCR2.1-TOPO vector (Invitrogen) to give plasmid pMF153. The premature $P_{PIR}$ sequence contained in pMF153 was subjected to a second round of PCR using primers OMF69: GATCGACGTCG-
GAGAAATAGCGCTGTACAGCGTATGG-
GAATCTcttgtacggtgtaCgagt atc (SEQ ID NO:7) and OMF57 described above. The resulting PCR fragment containing the complete $P_{PIR}$ sequence was cloned into pCR2.1-TOPO in lacZ orientation to give pMF161. The annealing sequence of OMF69 (small letters) is complementary to the extension of OMF62 (capital letters) and adds the remaining Pip binding site of $P_{PTR}$ to $P_{PIR}$.
Construction of the Pristinamycin-Responsive Reporter Plasmids pMF164 and pMF172 and the pTWIN Vectors For the construction of pMF164 the $P_{PIR}$-containing fragment was excised from pMF161 by AatII and EcoRI and ligated to the corresponding sites (AatII/EcoRI) of the GFP expression vector pMF104, thereby replacing the TET-responsive promoter $P_{hCMV*-1}$ (Fussenegger et al., 1998, supra). Similarly, pMF172 was constructed for quantitative analysis of $P_{PIR}$-mediated expression, by exchanging $P_{hCMV*-1}$ of pMF111 (Fussenegger et al., 1997, Biotechnol. Bioeng. 55, 927–939) by $P_{PIR}$ of pMF164 via SspI and EcoRI.

pTWIN contains both PIT and tTA in a $P_{SV40}$-driven dicistronic configuration. For construction of pTWIN, PIT was first transferred from pMF156 as an EcoRI/HindIII fragment to the corresponding sites of pSBC-1 (EcoRI/HindIII; resulting in pMF167) before the PIT expression unit could be fused to the tTA expression unit contained on pSBC2-tTA (Fussenegger et al., 1997, supra) via SspI/NotI sites. Thus, pTWIN contains the dicistronic $P_{SV40}$-PIT-IRES-tTA-pA expression cassette.
Cell Culture, Transfection, Construction of Stable Cell Lines, SEAP Activity Test and Gel Retardation Assays Chinese hamster ovary cells (CHO-K1, ATCC: CCL 61), Baby hamster kidney cells (BHK-21, ATCC: CRL-8544), and HeLa cells (ATCC: CRL-7923) as well as stable cell lines CHO-PIT1, CHO-PIT2, CHO-TWIN1$_{95}$, CHO-TWIN1$_{108}$ and CHO-PIT1-SEAP were cultured as described before (Fussenegger et al., 1998, Nat. Biotechnol. 16,468–472) in the presence of appropriate antibiotics: G418 400 µg/ml; zeocin 100 µg/ml. Optimized CaPO$_4$ protocols were used for high efficiency transient transfection of all cell lines (id). Transient transfected cells were routinely analyzed after 48 h for GFP or SEAP expression using fluorescence microscopy and p-nitrophenolphosphate-based light absorbance timecourse, respectively, as described before (Fussenegger et al., 1998, Nat. Biotechnol. 16, 468–472; Berger et al., 1988, Gene 66, 1–10 b). For construction of stable CHO-PIT and CHO-TWIN cell lines, CHO-K1 was cotransfected either with pMF156 or pTWIN1 and pSV2neo carrying the G418 resistance gene. CHO-PIT1-SEAP was constructed by cotransfection of pMF172 and pZeoSV2 (Invitrogen). For assessment of dose-response characteristics of $P_{PIR}$-regulated gene expression, CHO-PIT1-SEAP were cultured at cell densities of 150,000/ml for 48 at various PI concentrations. The mixed populations were cloned using FACS-mediated single-cell-sorting (FACStar$^{Plus}$; Beckton Dickinson). Gel retardation assay were performed as described (Salah-Bey et al., 1995, supra) using Pip purified from an overproducing strain of E. coli. Pip (0.02 pmol) was titrated with a range of antibiotic concentrations in a reaction volume of 20 µl. Protein solutions were pre-incubated at room temperature for 15 min. in the absence or presence of PI or its derivative quinupristin in a buffer containing 10 mM Tris (pH 7.8), 10 mM MgCl$_2$, 300 mM NaCl, 2 mM DTT and 10% glycerol. An EcoRI-HindII $P_{PTR}$ fragment (0.02 pmol) containing three Pip binding sites (radiolabelled using α-$^{32}$P)dATP was added and incubated for 15 min. To minimize nonspecific protein binding and increase protein stability, 2 µg of poly dIdC and 20 µg BSA were included in the incubation mix. Protein-DNA complexes were separated on 5% polyacrylamide, TBE gels and visualized by autoradiography.
Regulating Streptogramins Five different sources of pristinamycin were used: The two therapeutic forms Pyostacin™ and Synercid™, pristinamycin discs, and the single compounds pristinamycin I (PI) and pristinamycin II (PII). Pyostacin™ pills (500 mg) were ground in a mortar and solubilized in DMSO or water at a stock concentration of 50 mg/ml. Synercid™ (RP 59500; Lot Nr. CB06253) was provided by Aventis in injection-ready vials containing 500 mg lyophilized antibiotic which was reconstituted in 5 ml of 5% glucose solution and frozen at −20° C. Individual pristinamycin compounds PI and PII (identical to virginiamycin M$_1$ (VM$_1$); Sigma ref. V2753) were solubilized in DMSO at a concentration of 50 mg/ml and kept at −20° C. Antibiotic discs containing 15 µg pristinamycin or virginiamycin (bioMerieux, ref. 54552; bioMerieux, ref. 54612) were soaked in 1 ml cell culture medium at 4$_i$C for up to 24 h. Virginiamycin consists of virginiamycin S$_1$ (VS$_1$), the PI analogue, and virginiamycin M$_1$, which is identical in structure to PII (Barri re et al., 1994, supra). 2 µg/ml of streptogramin B was routinely used for regulation studies in cell culture. The concentration of individual streptogramin components was calculated based on their fixed 70:30 ratio (w/w; PII/VM$_1$/dalfopristin: PI/VS$_1$/quinupristin). For control experiments TET and doxycycline (DOX) were used either as discs (30 µg/disc, bioM□rieux ref. 54882 (TET) and ref. 54172 (DOX)) or as powder (Sigma refs. T3383 and D9891).

RESULTS
Construction and Functional Studies of the Streptogramin-Based Gene Regulation System in CHO Cells Gel retardation assays using purified Pip protein and a DNA fragment containing $P_{PTR}$ target sequence indicated a strong in vitro interaction between both elements in the absence of pristinamycin 1. However, in the presence of PI, Pip was completely released from $P_{PTR}$ (FIG. 1). $P_{PTR}$ of S. pristinaespiralis contains 3 dyad symmetrical binding sites (FIG. 1; lane A; $P_{PTR}$ in the absence of Pip) all of which are saturated at relatively large amounts of purified Pip (0.4 pmol; lane A) resulting in a single shifted band. Smaller amounts of Pip (0.02 pmol) presented an intermediate situation in which all possible permutations of site occupancy are represented in three distinct retarded bands (lane C). Pip (0.2 pmol lanes D–M) was titrated with a range of PI from 50 pmol to 0.01 pmol (lanes D–H; D: 50 pmol; E: 10 pmol; F: 1 pmol; G: 0.1 pmol; H: 0.01 pmol). Pip was completely released from $P_{PTR}$ by excess molar concentrations of PI. Under identical conditions the semisynthetic PI derivative quinupristin shows only partial release of Pip from individual $P_{PTR}$ binding sites even at highest concentration (lanes I–M; I: 50 pmol; J: 10 pmol; K: 1 pmol; L: 0.1 pmol; M: 0.01 pmol). The relatively low Pip-releasing activity of quinupristin correlates with its lower efficiency in regulating the PIT/$P_{PIR}$ system (see Table 5, infra).

In order to analyze the potential of the Pip/$P_{PIR}$ system for the design of a novel mammalian gene regulation system, we adapted these Streptomyces regulatory elements for use in a eukaryotic context by construction of a set of two chimeric determinants: the PI-inhibited transactivator (PIT, Pip fused to the VP16 transactivation domain of the Herpes simplex virus; Triezenberg et al., 1988, supra) and the PI-responsive promoter ($P_{PIR}$) ($P_{PTR}$ fused to the minimal insect promoter $P_{hsp70min}$; Corces et al., 1984, supra). Following transfection of a $P_{PIR}$-driven GFP expression construct (pMF164) into CHO cells, no green fluorescence could be observed by fluorescence microscopy, indicating that no endogenous host factors activate $P_{PIR}$. GFP-expression could only be detected when pMF164 was cotransfected with PIT-encoding pMF156, showing that the chimeric PIT protein functions as a transactivator for $P_{PIR}$ in mammalian cells. Transactivation of GFP expression was strictly PIT-dependent and could not be achieved by cotransfection of pMF164 with vectors containing other transactivators such as the tetracycline- (TET-) or ecdysone-dependent transactivators (pUHD15-1 encoding the tetracycline-repressible transactivator tTA; pUHD17-1neo encoding the tetraycline-inducible reverse tTA (rtTA; Gossen et al., 1995, supra; pVgRXR encoding VgEcR and RXR which heterodimerize to form the ecdysone-dependent transactivator; No et al., 1996, supra). Also PIT did not activate GFP expression from TET- or ecdysone-dependent promoters (pMF104; pIND-GFP (Invitrogen)).

Addition of pristinamycin to the culture medium of CHO cells simultaneously transfected with PIT (pMF156) and a $P_{PIR}$-SEAP (human placental secreted alkaline phosphatase) reporter construct (pMF172) greatly decreases SEAP expression compared to a cotransfected culture without pristinamycin as shown in Table 2.

| Inducer | SEAP Production (%) |
|---|---|
| None | 100 |
| Pristinamycin (Pyostacin ®; 2 μg/ml) | 8.49 ± 0.7 |
| PI (2 μg/ml) | 7.90 ± 1.2 |
| PII (2 μg/ml) | 96.3 ± 3.2 |

Table 2: Regulation potential of pristinamycin (Pyostacin®) and the pristinamycin group B (PI) and group A (PII) compounds. CHO-K1 cells were simultaneously cotransfected with pMF156 (PIT) and pMF172 ($P_{PIR}$-SEAP) in the presence or absence of the inducer indicated. Reporter gene expression (SEAP) was assayed 48 hr later.

In addition, pMF206 (PIT2; Pip-p65) was cotransfected with pMF172 ($P_{PIR}$-SEAP) and the SEAP readout in the absence and presence of PI (2 μg/ml) was directly compared to CHO-K1 cells cotransfected with pMF156 (PIT; Pip-VP16) and pMF172 ($P_{PIR}$-SEAP). As shown in the following table, PIT2 mediates higher overall SEAP expression levels compared to the pMF156/pMF172 configuration in the absence of pristinamycin but basal expression levels in the presence of pristinamycin remain significantly higher.

|  | No Inducer | +PI (2 μg/ml) |
|---|---|---|
| CHO + pMF206 + pMF172 | 0.49 ± 0.04 | 0.31 ± 0.003 |
| CHO + pMF156 + pMF172 | 0.23 ± 0.007 | 0.03 ± 0.002 |

Table 3 (previous page): Comparison of the regulation characteristics of PIT and PIT2. CHO-K1 cells were simultaneously cotransfected with the plasmids indicated and the SEAP readout (slope of the p-nitrophenolphosphate-based light absorbance time courses) was determined in the presence and absence of pristinamycin 48 hr post transfection.

This experiment indicates that external pristinamycin can enter mammalian cells and exert control of PIT/$P_{PIR}$-regulated gene expression there. However, pristinamycin has no influence on expression levels of $P_{SV40}$ or $P_{CMV}$-driven SEAP expression constructs (data not shown). Interestingly, only addition of the group B streptogramin PI shows effective downregulation of PIT/$P_{PIR}$-mediated SEAP expression; PII did not display any significant repression activity. Similar PI-dependent gene expression using the PIT/$P_{PIR}$ system has also been observed in BHK-21 and HeLa cells (not shown). No deleterious effects on CHO cell morphology and growth were observed at PI concentrations of 2 μg/ml found to be effective for repression of the PIT/$P_{PIR}$ system. This is the same order of magnitude as tissue concentrations reached in antibiotic therapy. Only much higher PI concentrations (above 50 μg/ml) were toxic for CHO cells.

Stable Expression of PIT in CHO Cells

Two representative clones, CHO-PIT1 and CHO-PIT2, were chosen at random among 11 PIT-expressing CHO cell clones stably transfected with a constitutive PIT expression construct (pMF156). Both cell lines show no unusual cell morphologies and display similar growth behavior compared to wild-type CHO-K1 cells, indicating that sustained constitutive PIT expression does not have obvious deleterious physiological effects on CHO cells.

Transient transfection of CHO-PIT1 and CHO-PIT2 with a $P_{PIR}$-SEAP expression vector (pMF172) resulted in high level SEAP expression in the absence of PI and significant repression in the presence of 2 μg/ml PI as shown in Table 4.

|  | SEAP Production (%) | |
|---|---|---|
|  | −PI | +PI |
| CHO-PIT1 + $P_{PIR}$-SEAP (pMF172) | 100 | 7.50 ± 2.32 |
| CHO-PIT2 + $P_{PIR}$-SEAP (pMF172) | 100 | 12.7 ± 3.57 |

Table 4: Pristinamycin I- (PI) dependent SEAP production of PIT- (PI-dependent transactivator) expressing stable cell lines CHO-PIT1 and CHO-PIT2 transiently transfected with the SEAP-encoding, PI-responsive reporter plasmid pMF172.

Induction factors (the ratio of SEAP activity without PI to SEAP activity with PI) reach 13 and 8 for CHO-PIT1 and CHO-PIT2, respectively. PI-responsive SEAP regulation of both CHO-PIT derivatives is fully reversible following repeated cycles of addition and withdrawal of this streptogramin, indicating reversible PI-PIT interaction in mammalian cells. This characteristic is necessary to achieve fluctuating daily dosing regimes optimal for many therapeutic proteins such as insulin.

Dose-Dependence of PI-Mediated Gene Regulation in CHO Cells

Figure 2:
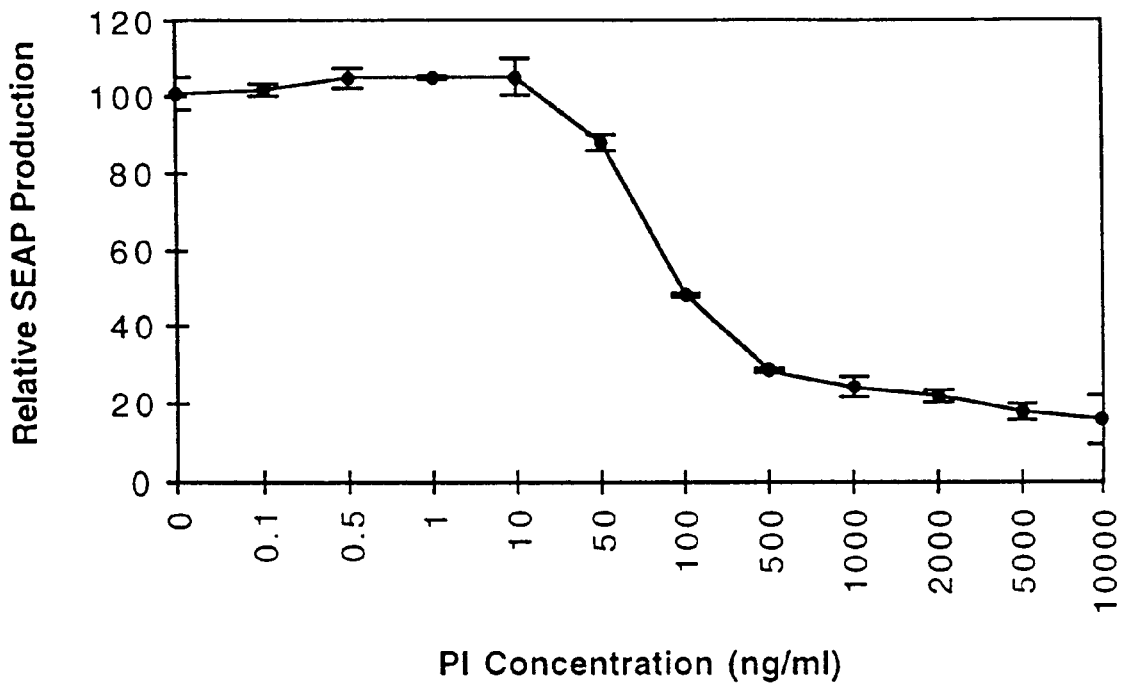
FIG. 2: Dose-response curve for PI-dependent gene expression. The cell line CHO-PIT1-SEAP was grown for 48 h at different PI concentrations (ng/ml). The relative SEAP production is shown over 5 orders of magnitude of PI concentration.

The levels of $P_{PIR}$-regulated gene expression could be controlled by varying the concentrations of PI used for induction. This was assessed using a stable CHO cell line (CHO-PIT1-SEAP) which expresses $P_{PIR}$-SEAP (pMF172) and contains also a constitutive PIT expression vector (pMF156). FIG. 2 shows the dose-response curve for PI-dependent SEAP expression of CHO-PIT1-SEAP cultures over 5 orders of magnitude of PI concentration. Beyond the concentration window of 10–500 ng/ml, the PIT/$P_{PIR}$ is either fully induced (<10 ng/ml) or repressed (>500 ng/ml), while gene expression can be adjusted to different levels within this window of concentrations. Increasing PI concentration above 10 ng/ml leads to a gradual decrease in SEAP expression, with lowest SEAP expression levels at PI concentrations over 500 ng/ml. Besides the response plateaus of the PIT/$P_{PIR}$ system at PI concentrations below 10 ng/ml and above 500 ng/ml, this system shows a broad window between these two concentrations in which the gene expression can be adjusted to intermediate levels. Such adjustable gene expression characteristics are particularly important for clinical applications which require titration of circulating proteins into the therapeutic range.

Regulation Efficiency of Different Streptogramins

Access to alternative effective streptogramins would expand the spectrum of regulating agents available for future use in human cell and gene therapy. Accordingly, several commercially available streptogramin sources were tested for their potential to regulate the PIT/$P_{PIR}$ system as shown below in Table 5. Among available streptogramins, virginiamycin proved to be the most efficient regulating agent, showing an induction factor of 32, almost three times higher than pristinamycin-based regulation.

|  | SEAP Production (%) |
| --- | --- |
| No streptogramin | 100 |
| Pristinamycin I | 8.06 ± 0.05 |
| Virginiamycin | 3.41 ± 0.47 |
| Synercid | 28.8 ± 3.73 |

Table 5: Regulation potential of different streptogramins. CHO-PIT1 was transiently transfected with the SEAP-encoding plasmid pMF172 and grown for 48 h in the absence or presence of different streptogramins at a concentration of 2 μg/ml of their group B component.

Virginiamycin is very similar in structure to pristinamycin, since its group A component virginiamycin $M_1$ is identical to PII and its group B constituent, virginiamycin $S_1$ ($VS_1$), differs from PI only by the lack of a dimethylamine group.

Figure 3:
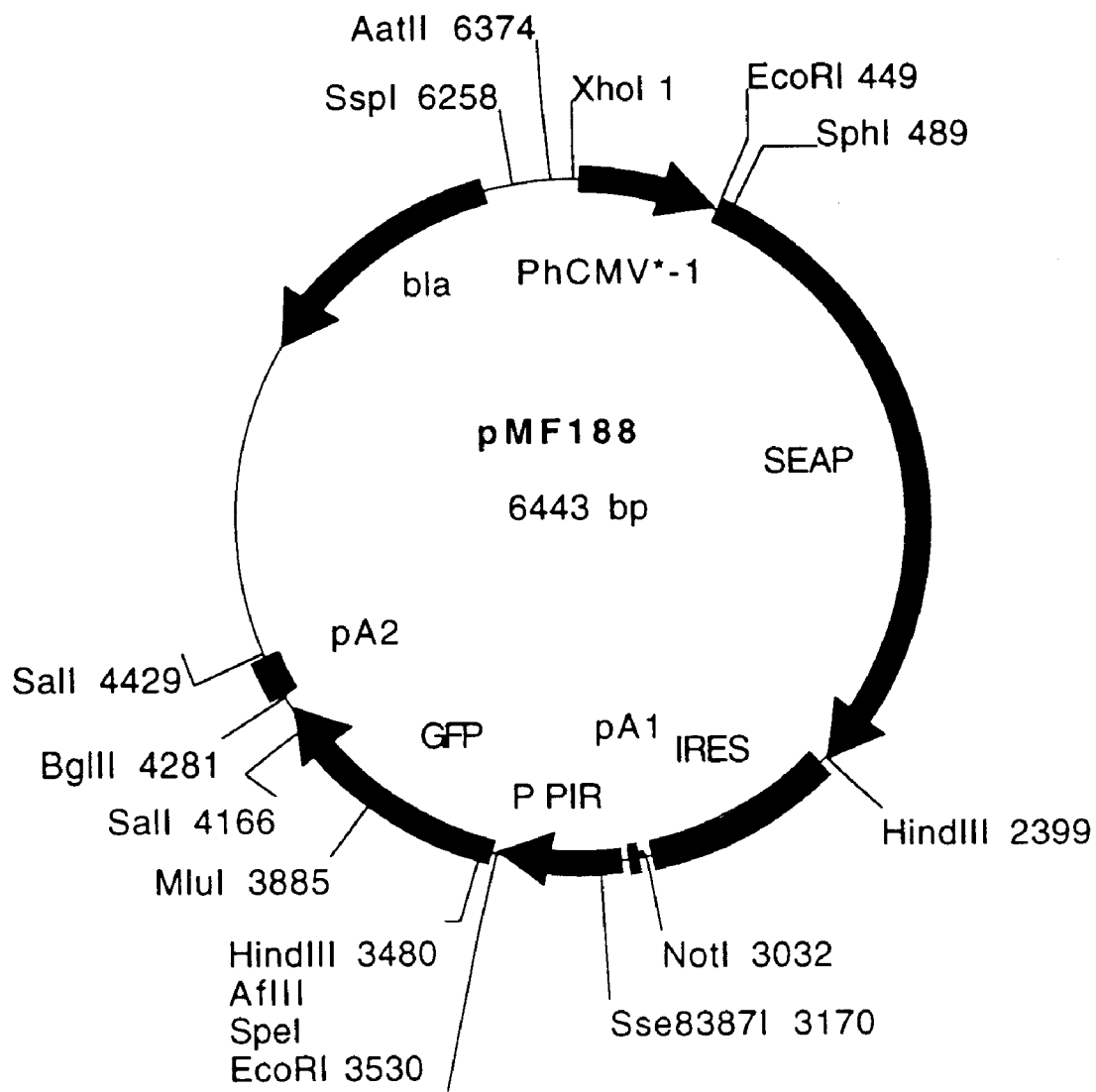
FIG. 3: Graphical representation of pMF188, a vector that combines tetracycline-responsive SEAP (human secreted alkaline phosphatase) and pristinamycin-responsive GFP expression in a single double regulated expression unit: $P_{hCMV^*-1}$-SEAP-pA$_I$-$P_{PIR}$-GFP-pA$_{II}$.

The improved antibiotic therapeutic potential of Synercid resides in its water solubility. Although Synercid was expected to achieve better control of the PIT/$P_{PIR}$ system due to its greater water solubility, its repression activity was almost 4-fold lower compared to Pyostacin and PI (Table 5). Apparently, the [(5δR)-[(3S)-quinuclidinyl]-thiomethyl modification of PI decreased the affinity of quinupristin to PIT, which is supported by gel retardation assays showing that quinupristin releases Pip from its target sequence $P_{PTR}$ less efficiently than PI (FIG. 3).

Comparison and Compatibility Studies of the Streptogramin- and Tetracycline-Based Gene Regulation Systems in CHO Cells The regulation performance of the PI-based regulation system was compared directly with the widely used TET-responsive expression concept. pTWIN1 encoding both PIT and the tetracycline-dependent transactivator tTA in a single constitutive dicistronic expression unit was stably established in CHO-K1 cells. Two representative clones out of 20 pTWIN1-containing clones, CHO-TWIN1$_{95}$ and CHO-TWIN1$_{108}$, were chosen for further studies. CHO-TWIN cells show the same cell morphology and similar growth behavior as wild-type CHO cells.

CHO-TWIN1$_{95}$ and CHO-TWIN1$_{108}$ were transfected under identical conditions with the isogenic plasmids containing the SEAP gene under control of the tTA-activated promoter $P_{hCMV*-1}$ (pMF111) or the PIT-activated promoter $P_{PIR}$ (pMF172). Transfected cells were grown for 48 h in the presence or absence of either antibiotic prior to assay of SEAP activity. Results are shown below in Table 6.

|  |  | SEAP Production (%) | |
| --- | --- | --- | --- |
|  |  | CHO-TWIN1$_{95}$ | CHO-TWIN1$_{108}$ |
| $P_{PIR}$-SEAP (pMF172) | No inducer | 100 | 100 |
|  | +PI | 8.84 ± 0.01 | 2.2 ± 0.4 |
|  | +VIR | 3.75 ± 0.39 | 1.2 ± 0.41 |
| $P_{hCVM*-1}$-SEAP (pMF111) | No inducer | 100 | 100 |
|  | +TET | 8.57 ± 0.37 | 7.56 ± 0.01 |

Table 6: Comparison of the regulation performance of streptogramin- (PI and virginiamycin; VIR) and tetracycline-based gene regulation systems. The two cell clones CHO-TWIN1$_{95}$ and CHO-TWIN1$_{108}$ containing both pristinamycin- and tetracycline-dependent transactivators were transfected with either the streptogramin-responsive or the TET-responsive SEAP reporter plasmids pMF172 ($P_{PIR}$-SEAP) and pMF111 ($P_{hCMV*-1}$-SEAP), respectively, and the relative SEAP production was assessed. SEAP production values are normalized by SEAP activities under the antibiotic-free, active promoter conditions as follows: pMF172 in CHO-TWIN195:1.7 mU/ml; in CHO-TWIN1$_{108}$: 1.8 mU/ml. pMF111 in CHO-TWIN1$_{95}$: 18.6 mU/ml; in CHO-TWIN1$_{108}$: 19.2 mU/ml.

The maximum SEAP expression levels of the TET-system were approximately 10-fold higher compared to the $P_{PIR}$-driven SEAP expression. This is expected since the different chimeric promoters involved differ in their minimal promoter elements. While the TET-promoter $P_{hCMV*-1}$ has been optimized by heptameric tTA binding elements to reach 35-fold higher expression levels than the precursor viral CMV promoter (Yin et al., 1995, Cancer Res. 55, 4922–4928), $P_{PIR}$ is in its unmodified, original "wild-type" configuration prior to any such refinements to increase fully-activated transcription. To analyze the relative regulatory characteristics, we evaluated induction factors (IF; ratio of maximal expression level to antibiotic-repressed expression level). IFs have been shown to remain largely unaffected by the choice of the minimal promoter or other promoter modifications aimed at increasing the maximum expression level (No et al., 1996, supra). While the PI- and the TET-system of CHO-TWIN1$_{95}$ exhibit nearly identical IFs of 12 in the SEAP reporter assay, CHO-TWIN1$_{108}$ displays 13-fold downregulation of SEAP in the presence of TET but downregulation by a factor of 45 by the addition of PI. Using virginamycin as regulating agent instead of PI for CHO-TWIN1$_{95}$ and CHO-TWIN1$_{108}$ transfected with the P$_{PIR}$-SEAP expression vector (pMF172) IFs are even higher (27 for CHO-TWIN1$_{95}$ and 83 for CHO-TWIN1$_{108}$) (Table 6). Therefore, the PIT/P$_{PIR}$-based mammalian gene regulation system shows superior gene inducibility characteristics than the TET system in CHO cells engineered to provide regulation of both systems.

The PI and the TET systems can be used for combined therapeutic applications requiring different control modalities for different transgenes since they are compatible and regulated by different therapeutic antibiotics for which large sets of clinical and pharmacokinetic data are available. Crossrepression of PI and TET (or the TET derivative doxycycline) on the other expression regulation system was evaluated for CHO-TWIN1$_{108}$ transfected separately with P$_{PIR}$-SEAP (pMF172) and P$_{hCMV^*-1}$-SEAP (pMF111) expression constructs, and the results shown in Table 7.

|  |  | SEAP Production (%) |
|---|---|---|
| CHO-TW1N1$_{108}$ + pMF111 | — | 100 |
| CHO-TW1N1$_{108}$ + pMF111 | +PI (2 µg/ml) | 94.8 ± 5.3 |
| CHO-TW1N1$_{108}$ + pMF111 | +PI (10 µg/ml) | 92.4 ± 7.9 |
| CHO-TW1N1$_{108}$ + pMF172 | — | 100 |
| CHO-TW1N1$_{108}$ + pMF172 | +TET (2 µg/ml) | 87.7 ± 1.76 |
| CHO-TW1N1$_{108}$ + pMF172 | +TET (10 µg/ml) | 57.5 ± 5 |
| CHO-TW1N1$_{108}$ + pMF172 | +DOX (2 µg/ml) | 77 ± 6.9 |
| CHO-TW1N1$_{108}$ + pMF172 | +DOX (10 µg/ml) | 50.5 ± 7.9 |

Table 7: Compatibility of the streptogramin- and tetracycline-based gene regulation systems. Crossregulation of pristinamycin (PI) and the tetracyclines doxycycline (DOX) and tetracycline (TET). The cell line CHO-TWIN1$_{108}$ which contains the tetracycline-dependent transactivator (tTA) as well as the pristinamycin-dependent transactivator (PIT) was transfected with the streptogramin-responsive reporter SEAP plasmid pMF172 (P$_{PIR}$-SEAP) or the tetracycline-responsive SEAP reporter plasmid pMF111 (P$_{hCMV^*-1}$-SEAP).

Figure 5:
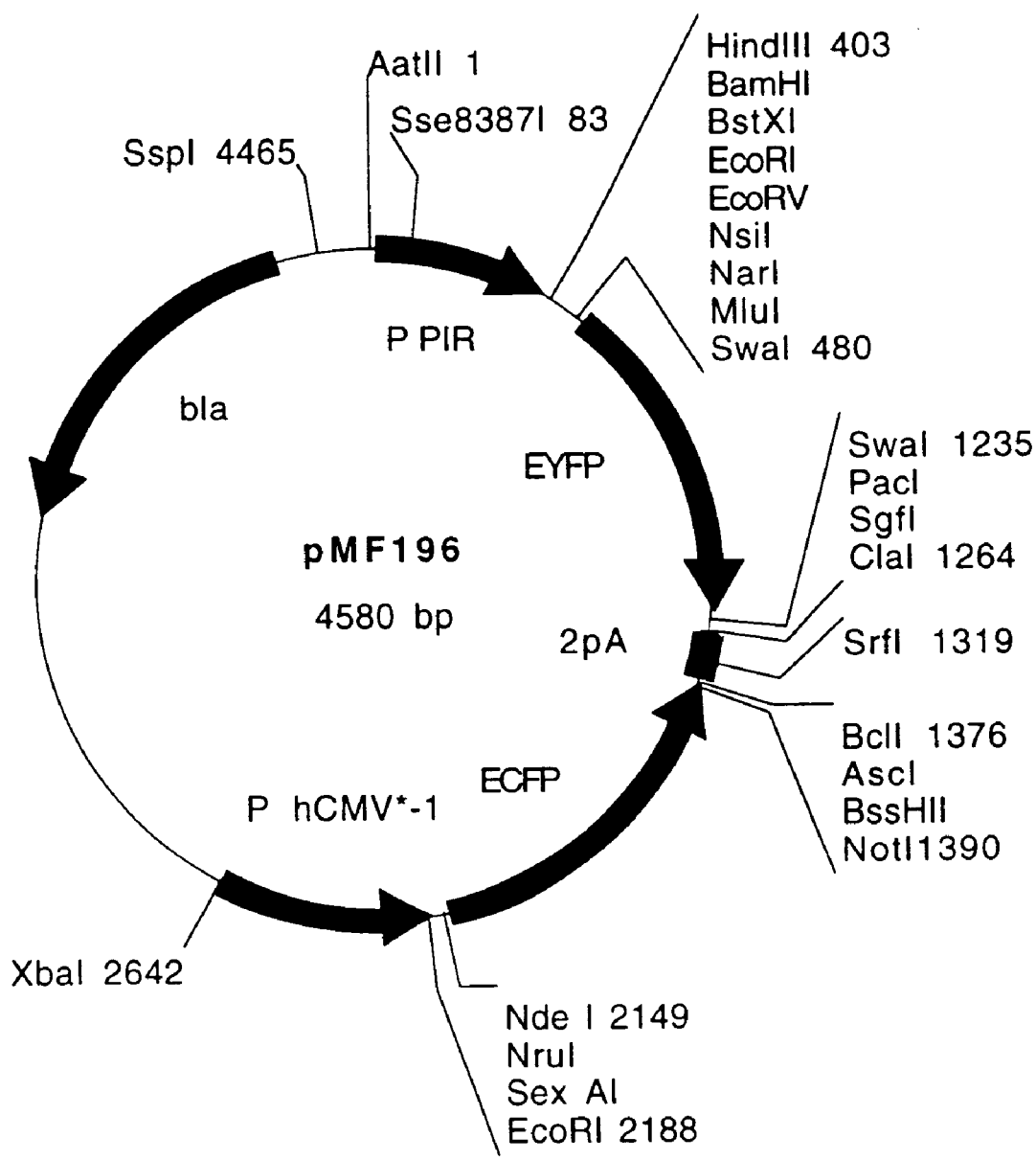
FIG. 5: Graphical representation of pMF196, a vector that is isogenic to pMF188 and pMF201 but contains the following double regulated expression unit: $P_{PIR}$-YFP-pA$_I$-pA$_{II}$s28-CFP-$P_{hCMV^*-1}$.

PI shows no effect on expression from the TET-responsive system. This experiment indicates that PI activation of SEAP expression in constructs containing PIT and P$_{PIR}$ operates by specific interaction of PI and PIT, as occurs between PI and the S. coelicolor protein Pip (Table 7; FIG. 5), and not via any generalized, nonspecific effect of PI on CHO cells.

Both tetracycline derivatives downregulate the PIT/P$_{PIR}$ system in a dose-dependent manner. However, at tetracycline concentrations commonly used for regulation of the TET-responsive promoter (2 µg/ml), the repressive effect of TET on the PIT/P$_{PIR}$ system is only 17%. This is sufficiently low that, for practical purposes, the TET- and Pip/P$_{PIR}$ systems provide essentially independently regulatable expression.

DISCUSSION

Properties of an ideal gene regulation system for therapeutic use include (i) low baseline expression and high induction ratio, (ii) control by a readily bioavailable, small-molecule drug showing no interference with host metabolism, (iii) high pharmacokinetic turnover of the regulating agent in all tissues to allow rapid reversion to the wild-type configuration, (iv) low potential for immune recognition, and (v) high modularity of regulation components to allow independent and efficient optimization as well as adaptation of the system to specific therapeutic situations. The streptogramin-based mammalian gene regulation system described here ideally satisfies these requirements. In cell lines engineered to afford control of both systems, the streptogramin-based regulation system shows over 10-fold lower baseline expression levels and up to 4-fold higher induction rations than the TET-responsive system. More importantly, streptogramins and tetracycline regulate their respective mammalian transcription systems essentially independently, showing that these two systems can be used together to achieve advanced therapeutic regimens in which to sets of transgenes can be regulated separately.

A whole set of streptogramin antibiotics, including the recently approved Synercid, are available with confirmed excellent bioavailability, pharmacokinetics and human compatibility. Also, streptogramin antibiotics are actively taken up by human cells, leading to regulation-effective concentrations in almost every part of the human body (Bebear, et al., 1997, J. Antimicob. Chemother. 39, 59–62). Nevertheless, streptogramin antibiotics are rapidly eliminated from the blood and most tissues, with half-lives typically not exceeding one hour in humans (Bergeron et al., 1997, J. Antimicrob. Chemother. 39, 129–138), ensuring ready reversibility of possible therapeutic conditions. The brain is the only site where virtually no streptogramin could be found following oral or intravenous application, since this class of antibiotics is unable to cross the blood-brain barrier (Bergeron et al., 1997, supra). This natural tissue-specific selectivity could allow straightforward brain-exclusive expression of the PIT/P$_{PIR}$ system in the presence of regulation-effective concentrations of streptogramin in the remaining body parts to enable design of therapeutic strategies for neurodegenerative diseases (Hardy et al., 1998, Science 282, 1075–1079).

A mammalian gene regulation system such as the PIT/P$_{PIR}$ configuration which responds to a class of chemically related antibiotics offers another powerful new dimension: finding new antibiotics which are urgently needed to cope with increasing prevalence of multidrug resistant bacterial pathogens. Metabolic libraries from Streptomyces or fungi could be screened using cultured mammalian cells containing the PIT/P$_{PIR}$ system linked to a reporter gene to identify novel streptogramins. This technology is at least one order of magnitude more sensitive than classical microbial inhibition tests and not biased by antibiotic resistance of indicator bacteria.

Additionally, the system described above can be adapted to use any of a number of different antibiotic resistance systems found in secondary metabolite/antibiotic producers within the Actinomycetes, particularly the Streptomyces. Examples of such systems that contain P$_{ptr}$-responsive promoters with cognate antibiotic binding proteins are the rifamycin-responsive gene cluster, the daunorubicin-responsive gene cluster, the landomycin-responsive gene cluster, the rapamycin-responsive gene cluster, and the tetracenomycin-responsive gene cluster.

EXAMPLE 2
The Double Regulation System

Most of today's gene therapy and tissue engineering strategies focus on stable integration of transgenes into human somatic cells either in vivo or ex vivo. While initial success was achieved using sophisticated gene transfer technology including attenuated viruses, site-specific recombination for targeted integration and nonimmunogenic selection markers, gene transfer is not the only challenge in future gene therapy and tissue engineering. However, the success and realization of this technology will largely dependent on flanking concepts which allow ex vivo expansion of grafted tissue followed by sustained growth control and reimplantation of treated cells or tissues. This concept requires two consecutive steps of opposite proliferation control which enables first expression of genes which activate proliferation for ex vivo expansion of tissue cells followed then by gene therapeutic operation and activation of proliferation control to allow reimplantation of genetically engineered tissue.

Using two human-compatible gene regulation systems, the tetracycline- and the pristinamycin-responsive system we set out to construct a double regulation system to achieve completely externally controlled proliferation management of mammalian cells.

MATERIALS AND METHODS

Figure 6:
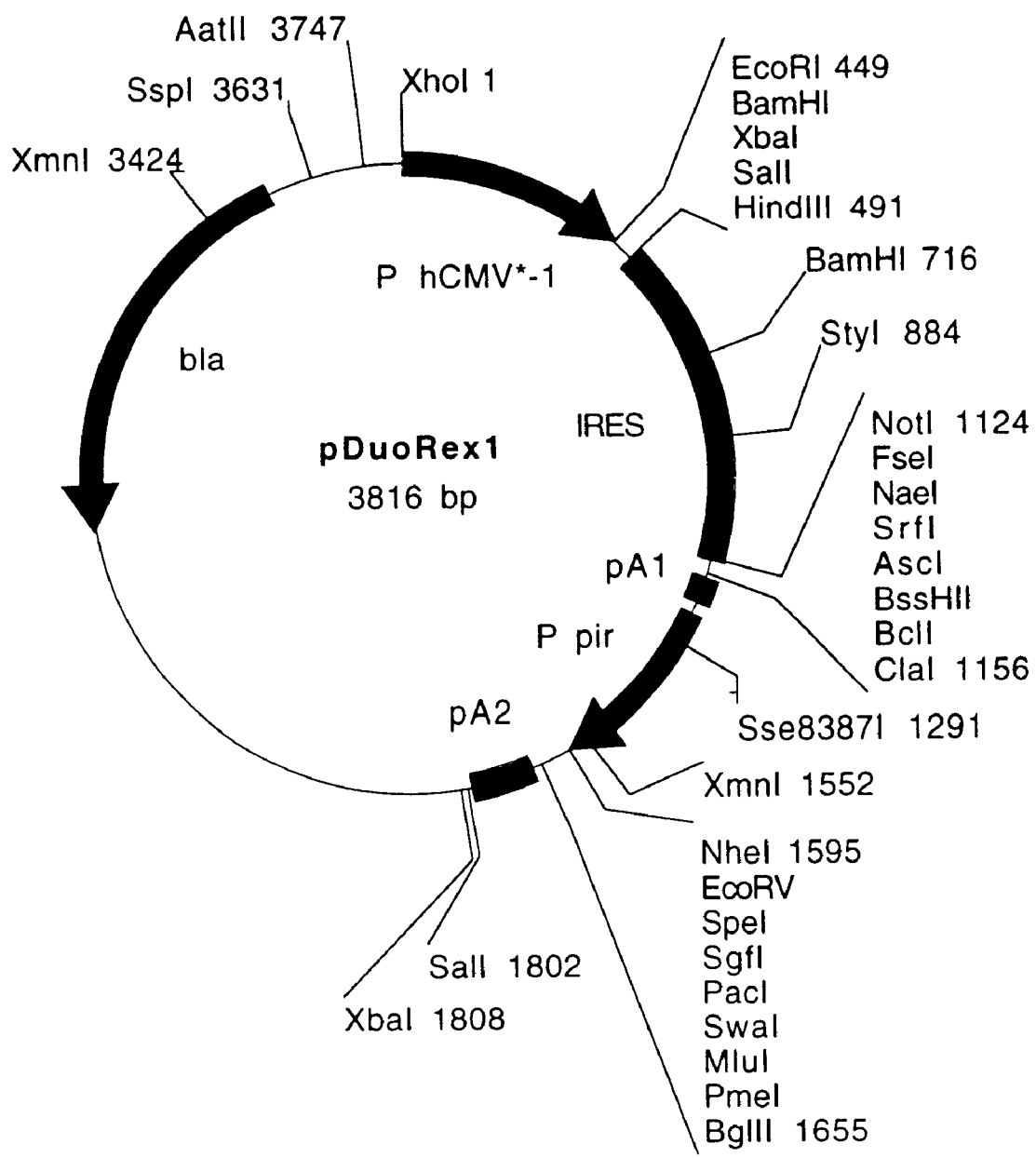
FIG. 6: Graphical representation of vector pDuoRex1. pDuoRex1 contains two expression units which allow independent adjustable gene expression in mammalian cells using tetracycline and pristinamycin as regulating agents. The tetracycline-responsive expression unit is driven by P followed by an internal ribosomal entry site (IRES) flanked by two multiple cloning sites. The expression unit contains a terminal artificial polyadenylation sequence (pA1). The IRES element enables dicistronic $P_{hCMV^*-1}$-driven expression. The second regulatable cistron is driven by $P_{PIR}$ followed by a multiple cloning site and terminated by a second polyadenylation sequence.

In order to construct the double regulatable mammalian expression vector pDuoRex1 a $P_{PIR}$-PA containing fragment was first amplified from pMF164 ($P_{PIR}$-GFP expression construct) using oligonucleotides OMF87: GATCACTAGTGATATCgctagctgtgtgagttc (SEQ ID NO:8) and OMF86: GATCGGATCCATCGATAATAAAATATCTTTATTTTCATTACATCTGTGTGTTGGTTTTTG TGTGcgtcggagaaatagcgc (SEQ ID NO:9). OMF86 contains in its 5' extension an artificial polyadenylation site (Levitt et al., 1989, Genes Dev. 3: 1019–1025) optimized to eliminate restriction sites. Also, OMF87 and OMF86 contain in their 5' extensions SpeI and ClaI sites (bold), respectively. The $P_{PIR}$-pA-containing fragment was cloned into pcDNA3.1/V5/His-TOPO (Invitrogen) in anti-$P_{CMV}$ orientation to give plasmid pSAM224. The $P_{PIR}$-pA-containing cassette was released from pSAM224 by restriction with SpeI and ClaI and cloned into the corresponding sites (SpeI/ClaI) of pTRIDENT1 to replace IRESII to result in pDuoRex1. As shown in FIG. 6, pDuoRex1 consists of the following double regulated expression unit: $P_{hCMV^*-1}$-MCSI-IRES-MCSII-pA$_I$/-$P_{PIR}$-MCSIII-pA$_{II}$ ($P_{hCMV^*-1}$, tetracycline-regulated promoter; MCS, multiple cloning site, IRES, internal ribosomal entry site; pA, polyadenylation site; $P_{PIR}$, pristinamycin-responsive promoter).

Figure 7:
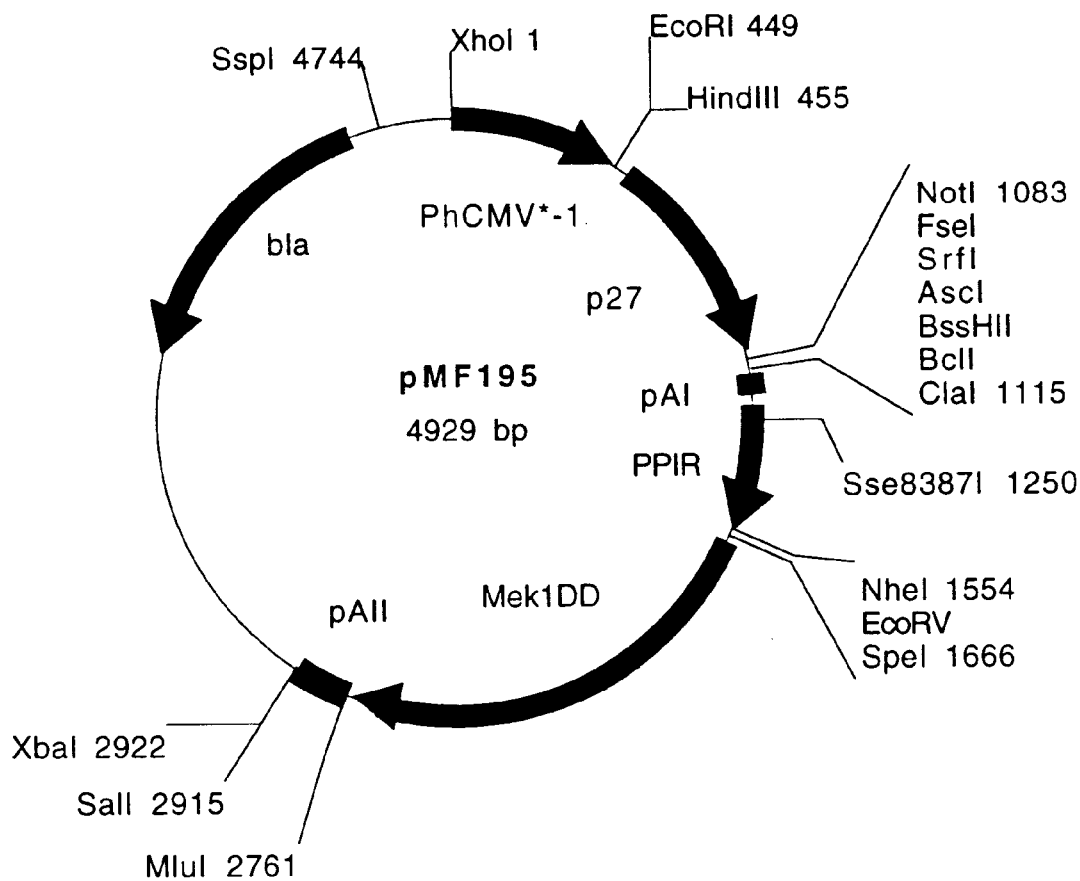
FIG. 7: Graphical representation of vector pMF195. PMF195 is a pDuoRex1 derivative containing the tumor suppressor gene p27 under control of the tetracycline-responsive promoter $P_{hCMV^*-1}$ and the Mek1 gene under control of $P_{PIR}$. Mek1 is a central kinase of the main growth factor signalling pathway and was particularly mutated (Mek1DD) to be constitutively active even in the absence of exogenous growth factors. Mek1 is an example of a class of proteins which promote cell proliferation.

Double regulation of Mek1DD, a constitutively active protein kinase of the central mammalian growth factor signaling pathway and the cyclin-dependent kinase inhibitor (CDI) p27 using pDuoRex1 was achieved by a 4-step cloning procedure: (1) Mek1DD was amplified from (pGem-Mek1DD; Greulich and Erikson, 1998, J. Biol. Chem. 273:13280–13288) by OMF92: GATCGATATCACTAGTCGCCACCatgcccaagaagaagcc (SEQ ID NO:10) and OMF93: GATCGGATCCACGCGTtcagatgctggcagcgtg (SEQ ID NO:11) and the 1.3 kb fragment was cloned into pcDNA3.1/V5/His-TOPO under control of the $P_{CMV}$ promoter to give pMF192. (2) p27 was amplified (from pDD6; Fussenegger et al., 1998) with OMF94: GATCGAATTCAAGCTTgcggtcgtgcagacccgg (SEQ ID NO:12) and OMF95: ATGCATCGATGCGGCCGCttacgtttgacgtcttctg (SEQ ID NO:13) and the 600 bp was cloned into pcDNA3.1/V5/His-TOPO under control of $P_{CMV}$ to give pMF193. (3) p27 was excised from pMF193 by EcoRI and NotI (contained in OMF94 and OMF95, respectively (bold)) and cloned into the corresponding sites of pDuoRex1 (EcoRI/NotI) thereby replacing the IRES-containing fragment and placing p27 under control of $P_{hCMV^*-1}$ to result in plasmid pMF194. (4) pMF192 was restricted with SpeI and BamHI (contained in OMF92 and OMF93, respectively (bold)) and Mek1DD was transferred to pMF194 linearized by SpeI and BglII thus placing Mek1DD under control of $P_{PIR}$ to give plasmid pMF195. As shown in FIG. 7, pMF195 contains the following double regulated expression unit: $P_{hCMV^*-1}$-p27-pA$_I$/-$P_{PIR}$-Mek1DD-pA$_{II}$.

Additional double regulation vectors analogous to pMF195 (which contained p27-Mek1DD) were also constructed in which the Mek1DD gene coding sequence was replaced by other growth promoting genes. Specifically constructs containing sequences encoding the adenoviral large T antigen, the adenoviral small T antigen, and the human papillomavirus E7 protein under control of the $P_{PIR}$ promoter were constructed using well known techniques.

In a parallel cloning procedure pMF188 was cloned containing the $P_{hCMV^*-1}$-SEAP-IRES-pA$_I$-$P_{PIR}$-GFP-pA$_{II}$. GFP was amplified from pMF164 by OMF84 :GATCGCGGCCGCAATAAAATATCTTTATTTTCATTACATCTGTGTGTTGGTTTTT TGTGTGcgtcggagaaatagcgc (SEQ ID NO:14) and OMF85: GTACAGATCTtta tttgtagagctcatc (SEQ ID NO:15) and cloned into pcDNA3.1/V5/His-TOPO under control of $P_{CMV}$ to give plasmid pSAM223. Since OMF84 contains in its extension an artificial pA element pSAM223 contains a pA-GFP cassette which was excised by NotI and BglII (contained in OMF84 and OMF85, respectively (bold)) and cloned into the corresponding sites (NotI/BglII) of pMF124 (pTRIDENT3 containing SEAP in the first cistron) to give pMF188.

Figure 4:
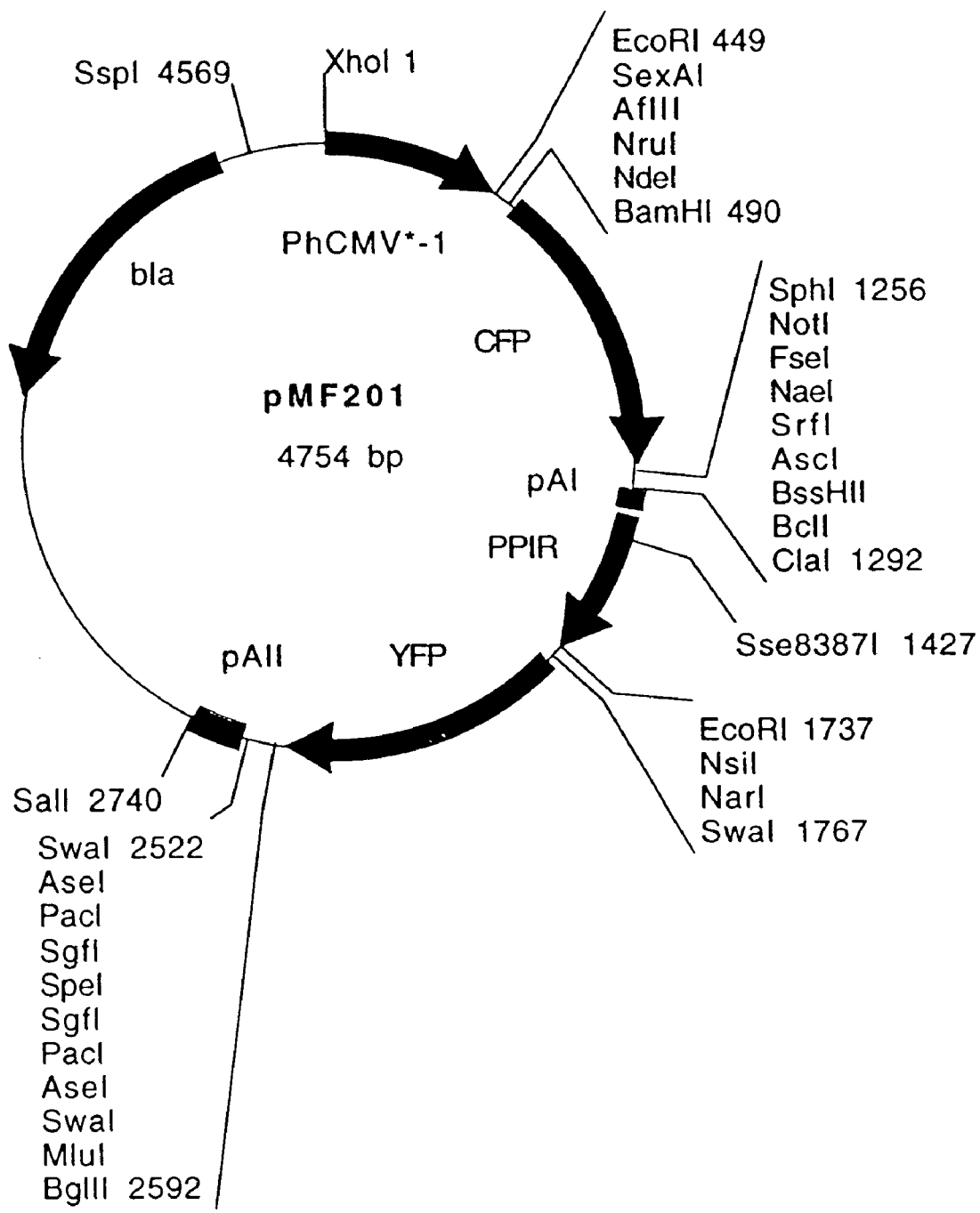
FIG. 4: Graphical representation of pMF201, a vector that contains tet-regulated CFP (cyan fluorescent protein) and pristinamycin-regulated YFP (yellowish fluorescent protein) in a single expression unit: $P_{hCMV^*-1}$-CFP-pA$_I$8-$P_{PIR}$-YFP-pA$_{II}$.

A further double regulated configuration was cloned for use in transgenic animals utilizing the two compatible GFP-derived fluorescent proteins, CFP (cyan fluorescent protein) and YFP (yellowish fluorescent protein) were combined in a pDuoRex1-derived expression vector by a 4-step cloning procedure: (1) CFP was amplified from pECFP-C1 (Clontech) with oligos OMF96:GATCGAATTCCCTCAGCACCAGGTCATG CTTAAGTCGCGACATATGgatcCgCta gcgctaccg (SEQ ID NO:16) and OMF89: GATCAAGCTTGCCCGGGCCACACAAA AAACCAACACAGATGTAAT-GAAAATAAAGATATTTTATTTGATCAG-GCGCGCCGCGGCC GCATGCttacttgtacagctcgtc (SEQ ID NO:17) and cloned into pcDNA3.1/V5/His-TOPO under control of $P_{CMV}$ to give plasmid pSAM228. (2) YFP was amplified from pEYFP-C1 (Clontech) with oligos OMF90:GTACGAATTCGATATCATGCATGGCGCC GTTTAAACGCGTATTTAAATgatccgc tagcgctaccg (SEQ ID NO:18) and OMF91: GATCAAGCTTGCGGCCGCG-GATCCG CCCGGGCCACACAAAAAACCAACACA-CAGATGTAATGAAAATAAAGATATTTTATTATCGA TACTAGTGCGATCGCTTAATTAATT-TAAATttacttgtacagctcgtcc (SEQ ID NO:19) and cloned into pcDNA3.1/V5/His-TOPO under control of $P_{CMV}$ to give plasmid pSAM222. (3). CFP was excised from pSAM228 by EcoRI and NotI (contained in OMF96 and OMF89, respectively (bold)) and cloned into the corresponding sites (EcoRI/NotI) of pDuoRex1 thereby replacing the IRES element to give pMF200. (4) pMF200 was linearized with EcoRV and SpeI ligated to YFP excised from pSAM222 by EcoRV and SpeI (contained in OMF90 and OMF91, respectively (bold)) to give pMF201. As shown in FIG. 4, pMF201 contains the following double regulated expression unit: $P_{hCMV^*-1}$-CFP-pA$_I$/-$P_{PIR}$-YFP-pA$_{II}$.

pMF196 is a CFP/YFP-containing double regulation construct similar to pMF201 but both expression units converge. Cloning of pMF196 required a 4-step cloning procedure: (1) The YFP-pA containing cassette was excised from pSAM222 by EcoRI and NotI and ligated to the corresponding sites of pMF164 (EcoRI/NotI) thereby replacing GFP of pMF164 to result in plasmid pSAM226 (2) The $P_{PIR}$-YFP-PA cassette was excised with SspI/NotI from pSAM226 and ligated into the corresponding sites pTRIDENT1 (SspI/NotI) thereby replacing $P_{hCMV*-1}$ and IRES I of pTRIDENT1 to give plasmid pMF190. (3) The CFP-pA cassette was excised from pSAM228 (OMF89 contains in it extension an artificial pA site) by EcoRI and HindIII (contained in OMF96 and OMF89, respectively) and ligated into the corresponding sites (EcoRI/HindIII) of pTBC1 (Dirks et al., 1993) to result in plasmid pSAM227. (4) The $P_{hCMV*-1}$-CFP-pA-containing cassette was released from pSAM227 by digestion with XhoI and SrfI and was ligated to pMF190 digested with SalI and SrfI to result in plasmid pMF196. As shown in FIG. 4 pMF196 contains the following double regulated expression unit: $P_{PIR}$-CFP-pA$_I$/pA$_{II}$-YFP-$P_{hCMV*-1}$.

RESULTS
Construction of Tetracycline- and Streptrogramin-Responsive Double Regulation Vectors In order to demonstrate the double regulation concept a set of three vectors were constructed (i) pMF188 combining tetracycline-responsive SEAP (human secreted alkaline phosphatase) and pristinamycin-responsive GFP expression in a single double regulated expression unit: $P_{hCMV*-1}$-SEAP-pA$_I$-$P_{PIR}$-GFP-pA$_{II}$ (FIG. 3). (ii) Similar to pMF188, pMF201 contains tet-regulated CFP (cyan fluorescent protein) and pristinamycin-regulated YFP (yellowish fluorescent protein) in a single expression unit: $P_{hCMV*-1}$-CFP-pA$_I$8-$P_{PIR}$-YFP-pA$_{II}$ (FIG. 4). (iii) pMF196 is isogenic to pMF188 and pMF201 but contains the following double regulated expression unit: $P_{PIR}$-YFP-pA$_I$-pA$_{II}$-CFP-$P_{hCMV*-1}$ (FIG. 5).

When these double regulation vectors were transiently transfected into CHO-TWIN1$_{108}$ cells all expression units contained on pMF188/pMF201/pMF196 showed independent on/off regulation regulation in response to the respective regulating antibiotics tetracycline and pristinamycin as monitored by SEAP activity tests and fluorescence microscopy. Based on experience with pMF188/pMF201/pMF196 we designed a multipurpose double regulation vector pDuoRex1 for use in tissue engineering and gene therapy (FIG. 6).

For the novel gene therapy and tissue engineering concept positive and negative proliferation control genes were carefully chosen. For negative proliferation control the use of tumor suppressor genes such as p21, p27, p53 or combinations thereof with differentiation factors such as c/ebpa and/or survival factors such as bcl-2 and bcl-x$_L$ in a multicistronic configuration is well-tested and reliable (Fussenegger et al., 1998). The choice of the positive proliferation control gene is important since its effect on engineered cells has to be sufficiently strong to induce resumption of the cell cycle in terminally differentiated cells but weak enough to allow reversion of the proliferating state and reimplantation of treated cells into the in vivo context.

We chose Mek1, a central protein kinase in the conserved mammalian Ras-MAP signal transduction pathway responding to growth-promoting signals such as cytokines. At the center of such signal transduction Mek1 not only transfers but also amplifies growth-promoting signals. Upstream kinases (Erk) phosphorylate Mek1 at two positions (serine 218) and (serine 222). A recently described double mutant contains two mutations which alter these ser218 and ser22 to aspartate and render Mek1DD constitutively active in the absence of upstream proliferation signals and in the absence of phosphorylation (Greulich and Erikson, 1998, J. Biol. Chem. 273: 13280–13288). Previous results by Greulich and Erikson, 1998) have shown that regulated overexpression of Mek1DD enables proliferation of NIH-3T3 cells in low serum. A pDuoRex1-based expression vector, pMF195, was constructed which contains p27 under control of $P_{hCMV*-1}$ and Mek1DD under control of $P_{PIR}$ (FIG. 7). Immunofluorescence analysis of CHO-TWIN1sub 108 transiently transfected with pMF195 show clear independent regulation of p27 and Mek1DD in response of the respective regulating antibiotic tetracycline and pristinamycin.

Besides Mek1DD other genetic determinants exerting positive control of mammalian cell cycle such as cyclins (erg. cyclin E) or E2F could also be envisioned. For example, double regulation vectors analogous to pMF195 (which contained p27-Mek1DD) were constructed in which the Mek1DD gene coding sequence was replaced by sequences encoding the adenoviral large T antigen, the adenoviral small T antigen, and the human papillomavirus E7 protein (all under control of the $P_{PIR}$ promoter). One can also use a sequence encoding the human papillomavirus E6 protein. In principle, this two gene double regulation concept can also be adapted to the multicistronic level to carefully fine tune expression of opposing proliferation control genes or to combine, for example, growth-inhibiting genes with genes such as c/ebpa which induce and maintain terminal differentiation. Also, monocistronic double regulation concepts could be foreseen which use sense and anti-sense expression of a single gene to induce or inhibit proliferation (or vice versa). Candidate genes include p27 anti-sense, expression of which has been shown to stimulate proliferation of quiescent fibroblasts and enable growth in serum-free medium (Rivard et al., 1996, J. Biol. Chem. 271: 18337–18341.), and nedd5 which is known as positive growth controlling gene (Kinoshita et al., 1997, Genes Dev. II: 1535–1547 but anti-sense expression may inhibit growth and leads to fried egg-like cell shapes as seen for cells arrested by overexpression of p27 (our own data not shown).

EXAMPLE 3
Promoter Modification to Enhance Maximal Expression from the Streptogramin-Responsive System In principle, every part of the PIT/$P_{PIR}$ system can be improved individually or exchanged by a more powerful component: (1) The Pip domain of PIT can be subjected to random mutagenesis to alter DNA binding affinity or specificity, to improve affinity to pristinamycin or other streptogramins or antibiotics or to reverse streptogramin responsiveness of the PIT/$P_{PIR}$ system (reverse PIT/$P_{PIR}$ system), for example allow induction of gene expression upon addition of pristinamycin instead of its withdrawal. (2) The VP16 domain could be exchanged by other transactivation domains such as the p65 domain of human NF-κB (Schmitz and Baeuerle, 1991, EMBO J. 10: 3805–3817) to "humanize" the regulation system and reduce immune recognition of PIT or the KRAB silencing domain of the human kox1 gene (Deuschle et al., 1995, Mol. Cell Biol. 15: 1907–1914) to construct a reverse PIT/$P_{PIR}$ system (these systems are under construction). (3) exchange of the minimal Drosophila heatshock promoter by other minimal promoters such as the minimal CMV promoter or the minimal promoter of the adenoviral E1B gene (also under construction).

The naturally occurring $P_{ptr}$ sequence contains only three distinct Pip binding sites which could accommodate PIT. In order to enhance maximal expression from streptogramin-responsive system, we constructed PI-responsive promoters with two ($P_{PIR2}$) and three ($P_{PIR3}$) ptr binding motifs with a total of 6 and 9 Pip binding sites, respectively.

Two synthetic DNA fragments were synthesized:
PPIR2 (SEQ ID NO:20): gacgtcgatatcGAAATAGCGCTG-TACAGCGTATGGGAATCTCTTGTACGGT- GTACGAGTA TCTTCCCGTACACCGTACGAAAT-
AGCGCTGTACAGCGTATGGGAATCTCTTGTAC
GGTGTA CGAGTATCTTCCCGTACACCGTACcctg-
caggand PPIR3 (SEQ ID NO:21): gacgtcgatatcGAAATAGCGCTG-
TACAGCGTATGGGAATCTCTTGTACGGT-
GTACGAGTA TCTTCCCGTACACCGTACGAAAT-
AGCGCTGTACAGCGTATGGGAATCTCTTGTACG
GTGTA CGAGTATCTTCCCGTACACCGTAC-
GAAATAGCGCTGTACAGCGTATGG-
GAATCTCTTGTAC GGTGTACGAGTATCTTCCCG-
TACACCGTACcctgcagg.

Both DNA fragments were digested with AatII and Sse8387I (corresponding restriction sites are shown in bold) and ligated to the corresponding sites of pMF172 ($P_{PIR}$-SEAP; AatII/Sse8387I) thereby replacing the single Pip binding sequence (Pptr of S. pristinaespiralis; Salah-Bey et al., 1995; Salah-Bey and Thompson, 1995) to result in plasmids pMF198 ($P_{PIR2}$-SEAP) and pMF199 ($P_{PIR3}$-SEAP).

All three PIT-dependent promoters $P_{PIR}$, $P_{PIR}2$ and $P_{PIR3}$ were cloned in front of a seap reporter gene to measure their transcriptional activity in the absence of pristinamycin (full induction). Table 8 shows relative expression profiles of $P_{PIR2}$ (PMF198; $P_{PIR2}$-SEAP) and $P_{PIR3}$ (pMF199; $P_{PIR3}$-SEAP) compared to "wildtype" $P_{PIR}$.

TABLE 8

Relative SEAP Expression from Modified $P_{pir}$-linked Genes

| | SEAP expression in the absence of PI | SEAP expression in the presence of PI |
|---|---|---|
| $P_{PIR}$-SEAP (pMF172) | 0.21 ± 0.01 | 0.04 ± 0.019 |
| $P_{PIR2}$-SEAP (pMF198) | 0.4 ± 0.05 | 0.073 ± 0.004 |
| $P_{PIR2}$-SEAP (pMF199) | 0.63 ± 0.009 | 0.09 ± 0.008 |

EXAMPLE 4

Construction of a Pristinamycin-Inducible Expression System with Enhanced Regulation Characteristics The Classical PIT/$P_{PIR}$ system belongs to the "OFF" family of regulation concepts since gene expression is activated upon withdrawal of the regulating antibiotic. However, in some applications such as gene therapy and tissue engineering an "ON" system which is induced upon addition of streptogramin antibiotics is more desirable. We therefore constructed a new Pip-based binary $PI_{ON}$ system which consists of a $P_{PIR}ON$ promoter and a set of two different transrepressors. $P_{PIR}ON$ consists of a PIR3 module containing 3 consecutive Pip binding elements (SEQ ID NO:21; Example 3) placed in front of the strong viral SV40 promoter. Transrepressors such as PIT3, which consists of a protein fusion between Pip and the KRAB silencing domain of the human kox-1 gene (Deuschle et al., 1995, Mol. Cell Biol. 15: 1907–1914) and PIT4, which is simply Pip expressed in a eukaryotic configuration, bind to PIR3 in front of $P_{SV40}$ and block transcription of this promoter. Besides sterical transcription blocking the silencing domain of PIT3 can additionally downregulate $P_{SV40}$ activity.

MATERIALS AND METHODS

The PIR3 sequence (SEQ ID NO:20) was excised from GeneOp™-PIR3 (the pUC-derived GeneOp expression vector is sold by Operon Technologies Inc.) by EcoRV and SmaI and ligated into the NruI site of pSEAP2-control (Clontech) thus resulting in plasmid pMF208 containing $P_{SV40}$-PIR3-SEAP cassette. The combination of $P_{SV40}$ and PIR3 is designated $P_{PIR}ON$.

PIT3, the Pip-KRAB fusion protein was constructed by a three step cloning procedure: (i) The KRAB domain of the human kox-1 gene was amplified from pSCTEVgal93Kox (Moosmann et al., 1997, Biol. Chem. 378: 669–677) with oligos OMF99:GATCGCGCGCC(AGATCCAAAAAAGAAGAGAAAGGT)(AGATCCAAAAAAGAAGAAAGGT)(AGATCCAAAAAAGAAGAGAAAGGT) AATGGATGCTAAG TCACTA (SEQ ID NO:25) and OMF100: GATCAAGCTTGGATCCTTACC AGAGAT-CATTCCTTGC (SEQ ID NO:26) and ligated in antisense orientation into pcDNA3.1/V5/His-TOPO (Invitrogen) to result in pMF203. OMF99 contains three consecutive nuclear localization signals (bracketed) derived from the SV40 large-T-antigen (Kalderon et al., 1984). (ii) The KRAB domain was excised from pMF203 by BssHII/HindIII and ligated to the corresponding sites (BssHII/HindIII) of pSBC2-tTA (Fussenegger et al., 1997) thus replacing the VP16 domain of tTA and resulting in pMF205. (iii) The tetR domain was excised of pMF205 by SspI/BssHII and replaced by Pip excised from pMF150 by SspI/BssHII to give plasmid pMF207. The resulting plasmid has the following PIT3 coding sequence:
ATGAGTCGAGGAGAGGTGCGCATGGC-
GAAGGCAGGGCGGGAGGGGCCGCGGGA-
CAGCGTGT GGCTGTCGGGGGAGGGGCGGCGCG-
GCGGTCGCCGTGGGGGGCAGCCGTCCGGGCT
CGACCG GGACCGGATCACCGGGGTCACCGTC-
CGGCTGCTGGACACGGAGGGCCT-
GACGGGGTTCTCG ATGCGCCGCCTGGCC
GCCGAGCTGAACGTCACCGCGATGTC-
CGTGTACTGGTACGTCGACA CCAAGGACCAGT-
TGCTCGAGCTCGCCCTGGACGCCGTCT-
TCGGCGAGCTGCGCCACCCGGA
CCCGGACGCCGGGCTCGACTGGCGCGAG-
GAACTGCGGGCCCTGGCCCGGGAGAACCGGGCG
CTGCTGGTGCGCCACCCCTGGTCGTC-
CCGGCTGGTCGGCACCTACCTCAA-
CATCGGCCCGC ACTCGCTGGCCTTCTC-
CCGCGCGGTGCAGAACGTCGTGCGCCGCAGC
GGGCTGCCCGCGCA CCGCCTGACCGGCGC-
CATCTCGGCCGTCTTCCAGTTCGTC-
TACGGCTACGGCACCATCGAG GGCCGCTTC-
CTCGCCCGGG
TGGCGGACACCGGGCTGAGTCCGGAG-
GAGTACTTCCAGGACT CGATGACCGCGGTGAC-
CGAGGTGCCGGACACCGCGGGCGTCATC-
GAGGACGCGCAGGACAT
CATGGCGGCCCGGGGCGGCGACACCGTG-
GCGGAGATGCTGGACCGGGACTTCGAGTTCGCC
CTCGACCTGCTCGTCGCGGGCATC-
GACGCGATGGTCGAACAGGCCTCCGCG-
TACAGCCGCG CGCCAGATCCAAAAAAGAA-
GAGAAAGGTAGATCCAAAAAAGAAGAGAAAG
GTAGATCCAAAAAAGAAGAGAAAGGTAATGGAT-
GCTAAGTCACTAACTGCCTGGTCCCGGA-
CACTGGTGACC TTCAAGGATGTATTTGTGGA
CTTCACCAGGGAGGAGTGGAAGCTGCTG-
GACACTGCTCAGC AGATCGTGTACAGAAATGT-
GATGCTGGAGAACTATAAGAACCTG-
GTTTCCTTGGGTTATCA
GCTTACTAAGCCAGATGTGA TCCTCCGGTTG-
GAGAAGGGAGAAGAGCCCTGGCTGGTGGAG
AGAGAAATTCACCAAGAGACCCATCCT-
GATTCAGAGACTGCATTTGAAATCAAATCATCAG
TTTCCAGCAGGGAGCATTTTTAAA-
GATAAGCAATCCTGTGACATTAAAATG-
GAAGGAATGGC AAGGAATGATCTCTGGTAA (SEQ ID NO:27).

For construction of PIT4, the Pip protein of Streptomyces coelicolor was amplified from pGemT::Epip4 with oligos OMF63:GTACGAATTCCCACCATGAGTCGAGGAGA GGTG (SEQ ID NO:1) and OMF103:GATCAAGCTTTCAGGCCTGTTCGACCATC (SEQ ID NO:28) followed by cloning into vector pcDNA3.1/V5/His-TOPO (Invitrogen) under control of $P_{CMV}$. The resulting plasmid pMF225 contains the following PIT4 sequence which corresponds to the sequence of the pip gene of Streptomyces coelicolor:

ATGAGTCGAGGAGAGGTGCGCATGGC-
GAAGGCAGGGCGGGAGGGGCCGCGGGA-
CAGCGTGT GGCTGTCGGGGGAGGGGCGGCGCG-
GCGGTCGCCGTGGGGGGCAGCCGTCCGGGCT
CGACCG GGACCGGATCACCGGGGTCACCGTC-
CGGCTGCTGGACACGGAGGGCCT-
GACGGGGTTCTCG ATGCGCCGCCTGGCCGC-
CGAGCTGAACGTCACCGCGATGTCCGTGTACT
GGTACGTCGACA CCAAGGACCAGTTGCTC-
GAGCTCGCCCTGGACGCCGTCTTCGGC-
GAGCTCGCCACCCGGA CCCGGACGC-
CGGGCTCGACTGGCGCGAGGAACTGCGGGCC
CTGGCCCGGGAGAACCGGGCG CTGCTGGT-
GCGCCACCCCTGGTCGTCCCGGCTG-
GTCGGCACCTACCTCAACATCGGCCCGC
ACTCGCTGGCCTTCTCCCGCGCGGTGCA-
GAACGTCGTGCGCCGCAGCGGGCTGCCCGCGCA
CCGCCTGACCGGCGCCATCTCGGC-
CGTCTTCCAGTTCGTCTACGGCTACG-
GCACCATCGAG GGCCGCTTCCTCGCCCGGG
TGGCGGACACCGGGCTGAGTCCGGAG-
GAGTACTTCCAGGACT CGATGACCGCGGTGAC-
CGAGGTGCCGGACACCGCGGGCGTCATC-
GAGGACGCGCAGGACAT
CATGGCGGCCCGGGGCGGCGACACCGTG-
GCGGAGATGCTGGACCGGGACTTCGAGTTCGCC
CTCGACCTGCTCGTCGCGGGCATC-
GACGCGATGGTCGAACAGGCCTGA (SEQ ID NO:29).

pMF150 is almost identical to pMF225 but the TGA stop codon of Pip encoded on pMF150 has been mutated in order to allow fusion to the various transactivating and transrepressing domains. Because of the mutation of this stop codon the pip gene contained in pMF150 is terminated a few bp downstream at the next stop codon encountered in the vector sequence. However, both Pip proteins perform equally in the PipON regulation concept.

RESULTS

Regulation Characteristics of the PipON System

CHO-K1 cells were cotransfected with pMF208 ($P_{PIR}$ON-SEAP) and either transrepressor-containing plasmid pMF207 (PIT3; Pip-KRAB) or pMF225 (PIT4; Pip). Cells were grown in the absence and presence of PI. In the absence of PI, expression of $P_{PIR}$ON was fully repressed and induction could be observed in the presence of PI. Table 9 shows the regulation characteristics of both inducible regulation concepts.

readout (slope a of the p-nitrophenolphosphate-based light absorbance time courses) was determined in the presence and absence of pristinamycin 48 hr post transfection. The SEAP expression levels of the PipON systems were compared to the pSEAP2-control construct which is isogenic to pMF208 but lacks the PIR3 binding element in front of the $P_{SV40}$ promoter.

While both PipON systems are induced in the presence of PI, their maximal as well as their basal expression levels differ significantly. Whereas the PIT4-$P_{PIR}$ON configuration (pMF225-pMF208) reaches expression levels comparable to the strong constitutive viral SV40 promoter and shows an induction factor of 25 which is more than double the induction factor of the classical PIT/$P_{PIR}$ system, the PIT3-PP RON configuration resulted in the tightest repression and an induction factor of about 150, more than 15 times higher compared to the PIT/$P_{PIR}$ system. However, the maximal expression level of the PIT-$P_{PIR}$ON configuration is about 3-fold lower compared to the maximal expression level of the PIT/$P_{PIR}$ configuration. The difference in their regulation characteristics enables the use of the two PIPON system for a broad range of different applications. In configurations which require high expression levels the use of the PIT4/$P_{PIR}$ON configuration is advantageous whereas situations which require tightest repression of basal expression of the transgene, the PIT3/$P_{PIR}$ON concept is the preferred system.

The modular setup of $P_{PIR}$ON consisting of an independent operator sequence (PIR3) and a fully functional promoter element allows straightforward exchange of PSV40 of $P_{PIR}$ON by any type of promoter to enable, for example, tissue-specific regulated expression or adaptation of this inducible regulation concept to other organisms such as yeast and plants.

Induction Potential of Different Streptogramin Antibiotics on the Pip/$P_{PIR}$ON Regulation System In order to assess the regulation potential of different streptogramin antibiotics, pMF225 or pMF150 encoding PIT4 were cotransfected with pMF208 ($P_{PIR}$ON-SEAP) into CHO-K1 cells and the SEAP induction was measured 48 following transfection (as described above in Example 1) and addition of the following streptogramin antibiotics: (i) PI, the group B streptogramin component of pristinamycin; (ii) Pyostacin, the human oral antibiotic; (iii) Synercid, the first injectable semi-synthetic pristinamycin derivative effective against most multidrug resistant human pathogenic bacteria and (iv) virginiamycin used as growth promotant in livestock feed. 2 µg/ml group B component was used for the regulation studies (for mixed streptogramins the concentration of the group B component was determined based on the fixed 70%: 30% ratio of group A and group B components).

Table 10 shows the induction potential of the different streptogramins. Pyostacin is as efficient in inducing the Pip/$P_{PIR}$ON as is pure PI component, virginiamycin exhibits slightly lower regulation performance and Synercid has almost no inducing capacity on the Pip/$P_{PIR}$ON system. Therefore, the use of Synercid in antibiotic chemotherapy is likely to be compatible with the use of the Pip/$P_{PIR}$ON system in gene therapy and tissue engineering applications.

|  | No Inducer | +PI (2 µg/ml) |
|---|---|---|
| CHO + pMF208 + pMF207 | 0.08 ± 0.006 | 0.00055 ± 0.0003 |
| CHO + pMF208 + pMF225 | 0.65 ± 0.03 | 0.019 ± 0.002 |
| CHO + pSEAP2-control | 0.67 ± 0.04 | |

Table 9: Comparison of the regulation characteristics of the PipON systems. CHO-K1 cells were simultaneously cotransfected with the plasmids indicated and the SEAP

|  | SEAP Production |
|---|---|
| No Streptogramin | 0.019 ± 0.002 |
| Pristinamycin I | 0.65 ± 0.03 |
| Pyostacin | 0.70 ± 0.005 |
| Synercid | 0.036 ± 0.0014 |
| Virginiamycin | 0.4125 ± 0.05 |

Table 10: Induction performance of different streptogramin antibiotics. CHO-K1 cells were simultaneously cotransfected with the plasmids pMF225 (PIT4) and pMF208 ($P_{PIR}$ON-SEAP) and the SEAP readout (slope of the p-nitrophenolphosphate-based light absorbance time courses) was determined in the presence and absence of the streptogramins indicated 48 hr post transfection.

EXAMPLE 5

Construction of Multi-Purpose Expression Vectors

Figure 8:
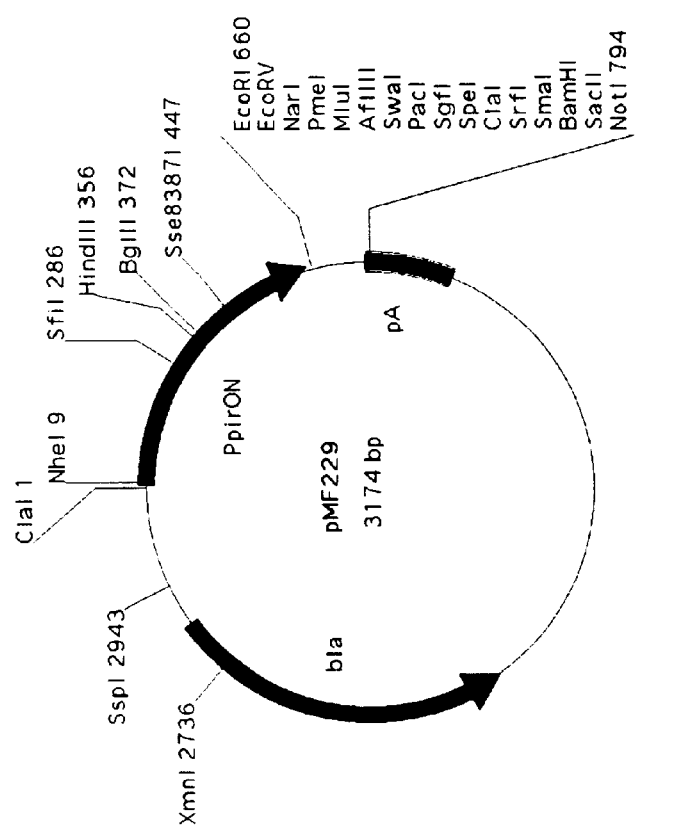
FIG. 8: Graphical representation of vectors pMF189 and pMF229.
Figure 8:
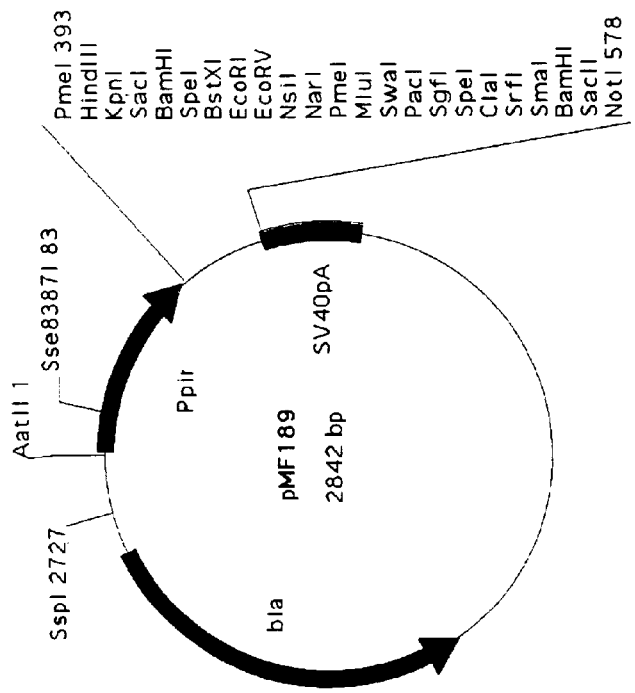

In order to use the pristinamycin-responsive mammalian gene regulation system in a wide variety of applications, a set of 6 mammalian gene expression vectors which are compatible with the use of all pristinamycin-dependent transactivators (PIT, PIT2) and transrepressors (PIT3, PIT4) was constructed. The first set of vectors, pMF189 and pMF229, consists of monocistronic expression vectors containing the $P_{PIR}$ (pMF189) and $P_{PIR}$ON (pMF229) promoters followed by a multiple cloning site of up to 22 unique restriction sites 6 of which are rare-cutting sites for enzymes recognizing 8 bp (FIG. 8).

Figure 9A:
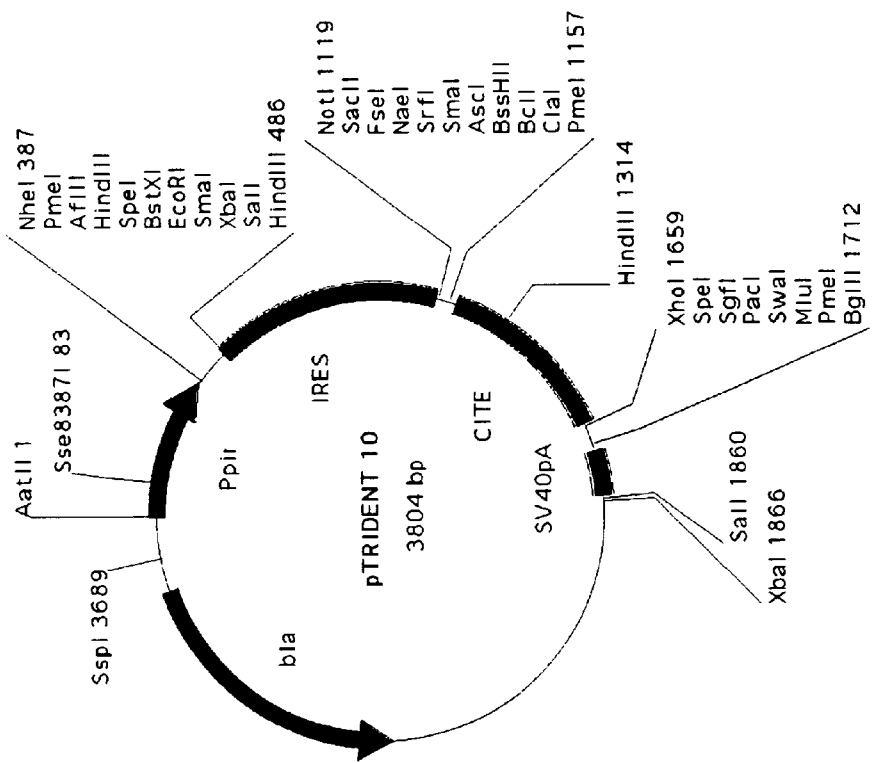
FIGS. 9A and 9B: Graphical representation of multicistronic vectors.
Figure 9B:
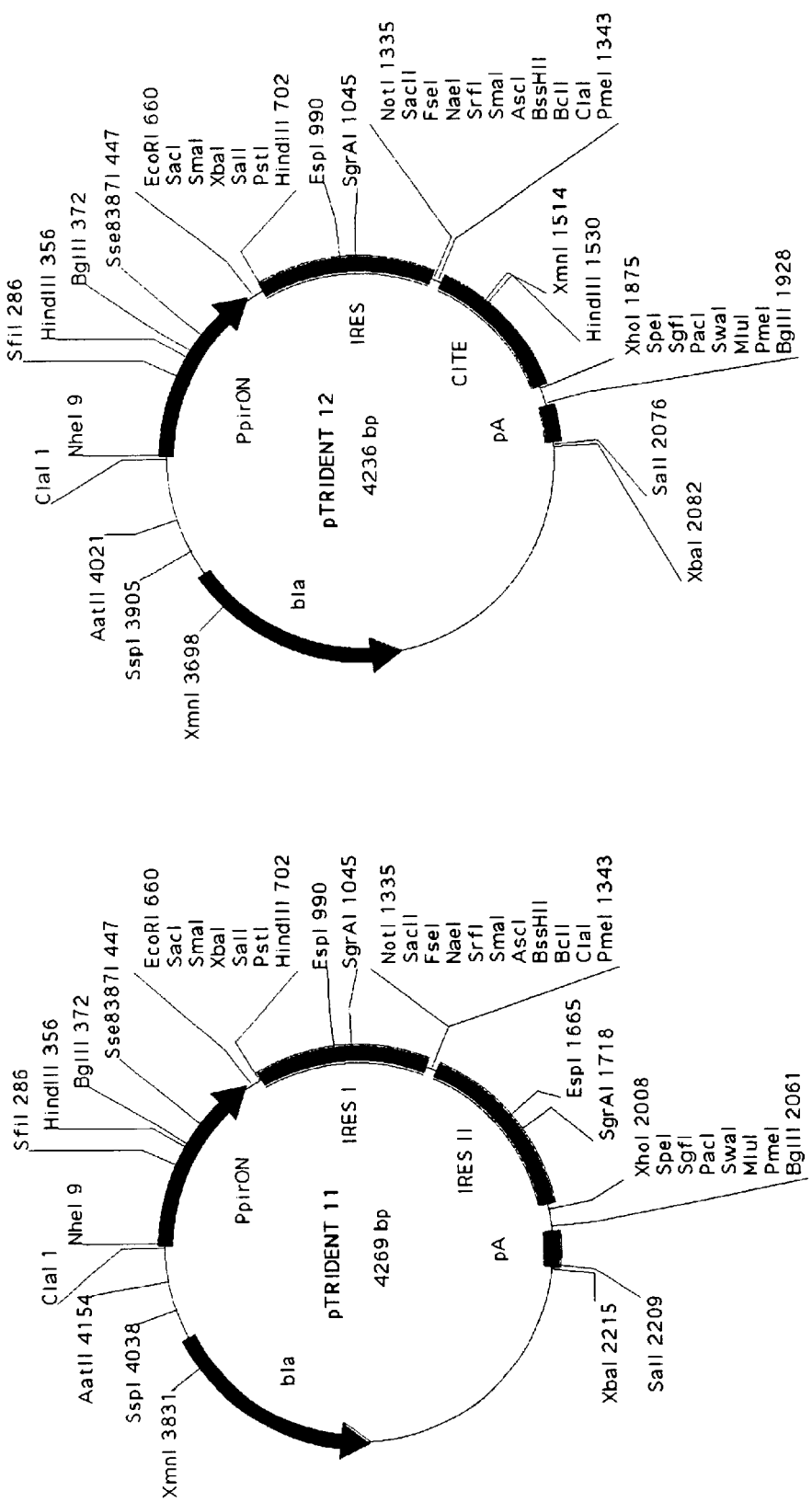

The second set of vectors is shown in FIG. 9 and contains the same promoters $P_{PIR}$ and $P_{PIR}$ON integrated in the pTRIDENT family of tricistronic expression vectors (Fussenegger et al. 1998, Biotechnol. Bioeng. 57,1–10). pTRIDENT vectors contain a single tricistronic expression unit which is driven either by $P_{PIR}$ (pTRIDENT9 and pTRIDENT10) or $P_{PIR}$ON (pTRIDENT11 and pTRIDENT12). While the first cistron is translated in the classical cap-dependent manner, the following two cistrons rely on cap-independent translation initiation mediated by internal ribosomal binding sites of the encephalomyocarditis virus or of polioviral origin (IRES). While pTRIDENT9 ($P_{PIR}$) and pTRIDENT11 ($P_{PIR}$ON) contain two IRES elements, pTRIDENT10 ($P_{PIR}$) and pTRIDENT 12 ($P_{PIR}$ON) contain an IRES as well as a CITE element. Both IRES elements are among the strongest currently available, showing high translation initiation in a wide variety of mammalian cells and tissues (Borman et al., 1997; Fussenegger et al., 1998, Biotechnol. Bioeng. 57,1–10, Fussenegger et al., 1998, Nat. Biotechnol-16,468–472). Both IRES elements are flanked by large polylinkers which allow convenient movement of genes into pTRIDENT derivatives. pTRIDENT vectors have proven to be useful tools for a wide variety of applications (Fussenegger et al., 1998, Biotechnol. Bioeng. 57,1–10; Fussenegger et al., 1998, Nat. Biotechnol. 16, 468–472).

Construction of Multi-Purpose Expression Vectors pMF189 the $P_{PIR}$ expression vector was constructed by a three step cloning procedure: (i) the yellowish fluorescent protein YFP was amplified from pEYFP-C1 (Clontech) with oligos OMF90: GTACGAATTCGATATCATGCATG-GCGCCGTTTAAACGCGTATTTAAAT-GATCCGCTAGCGC TACCG (SEQ ID NO:30) and OMF91:GATCAAGCTTGCGGCCGCGGATCCGCC CGGGCCACACAAAAAACCAACACACAGA TGTAAT-GAAAATAAAGATATTTTATTATCGATAC-TAGTGCGATCGCTTAATTAATTTAAAT TTACTTGTA-CAGCTCGTCC (SEQ ID NO:31) and ligated into pcDNA3.1/V5/His-TOPO to result in pSAM222. (ii) YFP was excised from pSAM222 by EcoRI/NotI and ligated to pMF164 (cut with EcoRI/NotI) thereby replacing GFP of pMF164 ($P_{PIR}$-GFP) and resulting in pSAM226 ($P_{PIR}$-YFP). (iii) YFP was eliminated from pSAM226 by SwaI and the remaining vector was religated to result in plasmid pMF189.

pMF229 was constructed by a three-step cloning procedure: (i) The PIR3 element was excised from pMF208 by XhoI/EcoRI and ligated to pTBC1 (XhoI/EcoRI) thereby replacing the tetracycline-responsive promoter $P_{hCMV*-1}$ of pTBC1 and resulting in pMF210. (ii) pMF210 was restricted with SspI/StuI and the viral SV40 promoter excised from pSBC1 with SspI/StuI was cloned in front of the PIR3 element to reconstitute $P_{PIR}$ON and result in plasmid pMF222. (iii) The $P_{PIR}$ON promoter was subsequently excised from pMF222 by SspI/EcoRI and ligated to pMF189 restricted with SspI/EcoRI thereby replacing $P_{PIR}$ of pMF189 with $P_{PIR}$ON and resulting in pMF229.

For construction of the tricistronic pTRIDENT expression vectors the $P_{PIR}$ promoter was excised from pMF164 by SspI/EcoRI and the $P_{PIR}$ON promoter was excised from pMF222 by SspI/EcoRI.

The $P_{PIR}$ promoter elements were subsequently cloned:
1. into the SspI/EcoRI sites of pTRIDENT1 to replace $P_{hCVM*-1}$ and result in pTRIDENT9 ($P_{PIR}$-MCSI-IRESI-MCSII-IRESII-MCSIII-PA).
2. into the SspI/EcoRI sites of pTRIDENT3 $P_{hCVM*-1}$ and result in pTRIDENT10 ($P_{PIR}$-MCSI-IRES-MCSII-CITE-MCSIII-PA).

The $P_{PIR}$ON promoter elements were subsequently cloned:
1. into the SspI/EcoRI sites of pTRIDENT1 to replace $P_{hCVM*-1}$ and result in pTRIDENT11 ($P_{PIR}$ON-MCSI-IRESI-MCSII-IRESII-MCSIII-PA).
2. into the SspI/EcoRI sites of pTRIDENT3 to replace $P_{hCVM*-1}$ and result in pTRIDENT12 ($P_{PIR}$ON-MCSI-IRES-MCSII-CITE-MCSIII-PA).

Construction of the Positive Feedback Regulation System Using the Streptogramin-Responsive Regulation Concept In contrast to the classical PIT/$P_{PIR}$ system in which PIT and $P_{PIR}$ reside on different plasmids, the positive feedback regulation concept places both elements in a single, often mutlticistronic, expression unit. In particular, the transactivator PIT is placed under control of its target promoter $P_{PIR}$.

In this configuration initial transcripts originating from the leakiness of the $P_{PIR}$ promoter lead to few PIT molecules which are inactivated in the presence of stregtogramins. However, in the absence of this class of antibiotics initial PIT molecules can bind to and induce $P_{PIR}$ Since a PIT transcript is produced in every round of transcription, a principle called positive feedback, PIT accumulates in the cell and ensures high-level expression of the transgene of interest, yet this system retains full regulatability. Advantages of the positive feedback regulation system over classical binary regulated expression systems are:

1. Tighter repression of gene expression since PIT is not expressed constitutively but originates from rare leaky transcripts. Therefore, in the repressed situation (in the presence of pristinamycin) little PIT is present in the cell which initiate transcription from $P_{PIR}$ in contrast to the situation in which PIT is constitutively expressed from a separate vector.
2. The positive feedback system produces a PIT molecule in every round of transcription leading to higher intracellular PIT levels and therefore also higher expression of the transgene of interest.
3. The positive feedback regulation concept establishes regulated gene expression in a single step. The classical binary PIT/$P_{PIR}$ expression systems requires first installation of PIT and then installation of the $P_{PIR}$-responsive gene. Two subsequent rounds of transfection and selection is not only tedious and time consuming but also undesired for advanced future therapies such as tissue engineering and gene therapy since the genome is changed significantly more than in a one-step engineering approach.

These positive feedback regulation vectors that were constructed contain both the green fluorescent protein GFP and PIT in a dicistronic, $P_{PIR}$-driven configuration. When pMF170 ($P_{PIR}$-GFP-IRES-PIT-pA) was transfected in CHO- K1, BHK-21 or HeLa cells bright green fluorescence could be observed by fluorescence microscopy in the absence of PI whereas GFP-expression was completely repressed in the presence of PI.

Also constructed was pTRIDENT-PIT (pMF175), which contains the pristinamycin-dependent transactivator in the first cistron of pTRIDENT9. Cistrons 2 and 3 of pTRIDENT-PIT could accommodate two different genes of interest. Therefore, pTRIDENT-PIT derivatives enable one-step installation of streptogramin-responsive expression of up to two independent genes.

Construction of the Positive Feedback Regulation Vectors

For construction of the autoregulatory system, PIT was excised from pMF156 by EcoRI/HindIII and cloned into the polylinker of the eukaryotic expression vector pSBC-2 (EcoRI/HindIII). As a pSBC-2 derivative, the resulting plasmid pMF169 is compatible to the pSBC-1 derivative pMF164 ($P_{PIR}$-GFP) and allows fusion of both expression units via their SspI/NotI restriction sites, thereby generating pMF170. pMF170 contains a dicistronic $P_{PIR}$-regulated expression unit encoding GFP in the first and PIT in the second cistron. Cap-independent translation initiation of the second cistron is enabled by a picornaviral internal ribosomal entry site (IRES) encoded upstream of PIT.

For construction of pTRIDENT-PIT, PIT was excised from pMF156 by EcoRI/HindIII and cloned into pTRIDENT1 was restricted with EcoRI/HindIII and PIT to result in plasmid pMF168. pMF168 was then restricted with SspI/EcoRI and the $P_{hCMV*-1}$ was replaced by PIR excised from pMF164 ($P_{PIR}$-GFP) with SspI/EcoRI to result in pMF175 which is designated pTRIDENT-PIT.

EXAMPLE 6
Detection of Novel Antibiotic Activities Using the Streptogramin-Responsive Expression Technology Streptogramins are unique antibiotics. Due to their composite nature (group A and group B streptogramins), they are less likely to elicit resistance mechanisms and show higher bacteriocidal acitivity because of a synergistic effect of both compounds. For example, one particularly useful streptogramin antibiotic is Synercid®, a semi-synthetic, injectable pristinamycin derivative, which is active against a wide variety of multidrug resistant human pathogenic bacteria including vancomycin-resistant species. Infections of these vancomycin-resistant specie are causing increasing health concerns in both the US and Europe.

A sensitive streptogramin detection technology will have two major impacts on current environmental and medical concerns: (i) Detection of trace amounts of banned streptogramins such as virginiamycin in the human food chain for inspection purposes and (ii) detection of novel streptogramin antibiotics in the culture supernatants of Actinomycetes and fungi.

RESULTS

The streptogramin detection technology is based on the pristinamycin-inducible (PipON) system (although the pristinamycin-repressible version can also be used) which has been established in mammalian cells (CHO-K1) stably or by cotransfection of pMF150 or pMF225 (Pip expression vector) and pMF208 ($P_{PIR}$ON-SEAP). The assay is based on the fact that presence of streptogramins in the test sample will induce the $P_{PIR}$ON promoter and lead to a quantitative change in the SEAP readout.

Using 100 microliters of *Streptomyces pristinaespiralis* (a major producer of pristinamycin) supernatant as standard, we compared the detection potential of the pristinamycin-responsive system to classical antibiogram tests using a collection of streptogramin-sensitive human pathogenic bacteria including *Staphylococcus aureus, Streptococcus pneumoniae, Streptococcus pyogenes, Listeria monocytogenes, Corynebacterium diphtheriae, Haemophilus influenzae* and *Neisseria gonorrhoeae* as well as the non-pathogenic *Bacillus sublilis* which is routinely used to screen for novel antibiotics effective against Gram positive bacteria. The presence of pristinamycin could be reliably detected in *S. pristinaespiralis* supernatants using the PipON system which resulted in about 20% of the SEAP readout typically reached using 2 µg/ml of pure pristinamycin 1. However, using the same amount of supernatant in antibiogram tests, antibiotic activity could only be detected in the hypersensitive strain of *C. diphtheriae* (19 mm of inhibitory diameter). All other pathogens tested including the standard antibiogram reference strain *B. subtilis* failed to detect pristinamycin in the *S. pristinaespiralis* supernatant despite of the synergy of streptogramins which has been reported to increase the bacteriocidal activity by a factor of 100 (Cocito et al., 1997, J. Antimicrob. Chemother. 39: 7–13).

Following efforts to detect new streptogramin derivatives we tested the culture supernatants of 14 novel Streptomyces isolates for the presence of antibiotic activity. Antibiogram analysis of the supernatants using *S. aureus, S. pyogenes, L. monocytogenes, C. diphteriae,* and *N. gonorrhoeae,* and 10 ml of culture supernatant, only two supernatants showed an antibiotic profile typical for streptogramins. One of these supernatants also induced the SEAP readout of the PipON system about 3-fold using only 100 microliters of supernatant which shows that the Pip-based streptogramin detection technology outperforms classical antibiogram test by at least a factor of 100. The second supernatant which was positive in the antibiogram test decreased the cell viability when applied to the PipON setup, indicating the potential antibiotic is cytotoxic to human cells. The correlation between antibiotic acitivity and induction of SEAP suggests that a novel Streptomyces species has been isolated which produces a streptogramine-like antibiotic activity.

The screening technology using the pristinamycin-responsive expression strategy has the following advantages over classical antibiogram tests: (i) Antibiotic screening is not limited by the sensitivity of indicator bacteria to a yet uncharacterized streptogramin (sensitivity of bacteria to antibotics greatly varies between strains and even isolates), (ii) the mammalian cell-based streptogramin detection concept shows at least two order of magnitude higher sensitivity to this class of antibiotics than antibiogram tests based on bacteriocidal activity, (iii) the mammalian screening context ensures exclusive detection of bioavailable and non-cytotoxic antibiotics.

The foregoing written specification is sufficient to enable one skilled in the art to practice the invention. Indeed, various modifications of the above-described means for carrying out the invention which are obvious to those skilled in the field of molecular biology, medicine or related fields are intended to be within the scope of the following claims. All references cited herein are incorporated by reference.

What is claimed is:

1. A host cell comprising:
    a) a nucleotide sequence to be transcribed operatively linked to a eukaryotic promoter and a $P_{abr}$ sequence; and
    b) a nucleic acid encoding a polypeptide which binds to said $P_{abr}$ sequence in the absence of its cognate antibiotic, wherein the nucleic acid hybridizes under high stringency conditions to a sequence that encodes the polypeptide encoded by SEQ ID NO:29, or the complement thereof.

2. The host cell of claim 1, wherein the nucleic acid hybridizes under high stringency conditions to the sequence of SEQ ID NO:29.

3. The host cell of claim 1 wherein the cognate antibiotic is a streptogramin.

4. The host cell of claim 3 wherein the streptogramin is pristinamycin.

5. The host cell of claim 1 wherein the nucleic acid encodes a polypeptide which binds to a $P_{abr}$ sequence in the absence of its cognate antibiotic operatively linked to a second polypeptide which activates or represses transcription in eukaryotic cells.

6. The host cell of claim 5, wherein the nucleotide sequence to be transcribed is endogenous to the host cell.

7. The host cell of claim 5, wherein the nucleotide sequence to be transcribed is exogenous to the host cell.

8. The host cell of claim 5, wherein the nucleotide sequence to be transcribed is a reporter gene.

9. The host cell of claim 8, wherein the reporter gene is SEAP or GFP.

10. The host cell of claim 5, wherein the polypeptide that activates transcription is selected from the group consisting of a VP16 activating domain, a GAL4 activating domain, a CTF/NF1 activating domain, an AP2 activating domain, an ITF1 activating domain, an ITF2 activating domain, an Oct1 activating domain, a Sp1 activating domain, and the p65 domain of NF-κB.

11. The host cell of claim 5, wherein the polypeptide that represses transcription is selected from the group consisting of a v-erbA oncogene product repressor domain, a thyroid hormone receptor repressor domain, a retinoic acid receptor repressor domain, a Drosophila Krueppel (Kr) protein repressor domain, a KRAB domain of the kox1 gene family, an even-skipped repressor domain, an S. cerevisiae Ssn6/Tup1 protein complex, a yeast SIRI protein, NeP1, a Drosophila dorsal protein, TSF3, SF1, a Drosophila hunchback protein, a Drosophila knirps protein, a WT1 protein, an Oct-2.1 repressor domain, a Drosophila engrailed protein, E4BP4, ZF5, a 65 amino acid repressor domain of E4BP4 and an N-terminal zinc finger domain of ZF5.

12. A method for regulating expression of a $P_{abr}$-linked gene in a eukaryotic cell, comprising:
    a) introducing into the cell a nucleic acid molecule encoding a $P_{abr}$-binding protein, wherein the nucleic acid hybridizes under high stringency conditions to a sequence that encodes the polypeptide encoded by SEQ ID NO:29, or the complement thereof, thereby rendering the $P_{abr}$-linked gene capable of regulation by an antibiotic that binds to the $P_{abr}$-binding protein; and
    b) modulating the amount of the antibiotic in the eukaryotic cell or in contact with the eukaryotic cell.

13. The method of claim 12, wherein the $P_{abr}$-binding protein further comprises an operably linked second polypeptide that activates or represses transcription in eukaryotic cells.

14. The method of claim 13, wherein the polypeptide that activates transcription is selected from the group consisting of a VP16 activating domain, a GAL4 activating domain, a CTF/NF1 activating domain, an AP2 activating domain, an ITF1 activating domain, an ITF2 activating domain, an Oct1 activating domain, a Sp1 activating domain, and the p65 domain of NF-κB.

15. The method of claim 13, wherein the polypeptide that represses transcription is selected from the group consisting of a v-erbA oncogene product repressor domain, a thyroid hormone receptor repressor domain, a retinoic acid receptor repressor domain, a Drosophila Krueppel (Kr) protein repressor domain, a KRAB domain of the kox1 gene family, an even-skipped repressor domain, an S. cerevisiae Ssn6/Tup1 protein complex, a yeast SIRI protein, NeP1, a Drosophila dorsal protein, TSF3, SF1, a Drosophila hunchback protein, a Drosophila knirps protein, a WT1 protein, an Oct-2.1 repressor domain, a Drosophila engrailed protein, E4BP4, ZF5, a 65 amino acid repressor domain of E4BP4 and an N-terminal zinc finger domain of ZF5.

16. The method of claim 12, wherein the $P_{abr}$-binding protein is obtained from *Streptomyces coelicolor*.

17. A method for regulating the expression of a $P_{abr}$-linked gene in a eukaryotic cell comprising the step of:
    modulating the level of an antibiotic in the eukaryotic cell or in contact with the eukaryotic cell, wherein said eukaryotic cell comprises the $P_{abr}$-linked gene and a nucleic acid molecule encoding a $P_{abr}$-binding protein, and wherein said nucleic acid molecule hybridizes under high stringency conditions to a sequence that encodes the polypeptide encoded by SEQ ID NO:29, or the complement thereof, and said antibiotic is capable of binding the $P_{abr}$-binding protein.

18. The method of claim 17 in which the $P_{abr}$-binding protein is operably linked to a polypeptide that activates or represses transcription in the eukaryotic cell.

19. The method of claim 12 or 17 wherein the antibiotic is a streptogramin.

20. The method of claim 19 wherein the streptogramin is pristinamycin.

21. A process for producing a protein comprising:
    culturing a eukaryotic cell containing:
        a $P_{abr}$-linked gene that encodes the protein and
        a nucleic acid molecule encoding a $P_{abr}$-binding protein, wherein the nucleic acid hybridizes under high stringency conditions to a sequence that encodes the polypeptide encoded by SEQ ID NO:29, or the complement thereof; and
    regulating expression of the $P_{abr}$-linked gene by modulating the level of an antibiotic that binds to the $P_{abr}$-binding protein in the cell or in contact with the cell.

22. The process of claim 21, further comprising the step of collecting the protein produced by the cell.

23. The process of claim 21 or 22, wherein the $P_{abr}$-binding protein further comprises an operably linked polypeptide that activates or represses transcription in eucaryotic cells.

24. The process of claim 21 wherein the antibiotic is a streptogramin.

25. The process of claim 24 wherein the streptogramin is pristinamycin.

* * * * *